United States Patent
Greenberg et al.

(10) Patent No.: US 11,339,222 B2
(45) Date of Patent: May 24, 2022

(54) KLRG1 ANTAGONIST SIGNALING THERAPY

(71) Applicant: The Brigham and Women's Hospital, Boston, MA (US)

(72) Inventors: Steven Greenberg, Watertown, MA (US); Stefano Vincenzo Gulla, Medford, MA (US); Kenneth Evan Thompson, Arlington, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 172 days.

(21) Appl. No.: 16/306,473

(22) PCT Filed: Jun. 2, 2017

(86) PCT No.: PCT/US2017/035621
§ 371 (c)(1),
(2) Date: Nov. 30, 2018

(87) PCT Pub. No.: WO2017/210523
PCT Pub. Date: Dec. 7, 2017

(65) Prior Publication Data
US 2019/0292264 A1      Sep. 26, 2019

Related U.S. Application Data

(60) Provisional application No. 62/401,557, filed on Sep. 29, 2016, provisional application No. 62/345,496, filed on Jun. 3, 2016.

(51) Int. Cl.
*A61K 39/395* (2006.01)
*C07K 16/28* (2006.01)
(Continued)

(52) U.S. Cl.
CPC ........ *C07K 16/2851* (2013.01); *A61K 39/395* (2013.01); *A61P 35/00* (2018.01);
(Continued)

(58) Field of Classification Search
None
See application file for complete search history.

(56) References Cited

U.S. PATENT DOCUMENTS 7,056,667 B2 *   6/2006   Lee ......................... C07K 14/47
                                                                435/6.16
10,556,007 B2 *  2/2020   Tripathi .................. A61P 27/02
(Continued)

FOREIGN PATENT DOCUMENTS

JP     2012025694 A  *  2/2012
WO    2016/070136 A1    5/2016
WO    2017/210523 A1   12/2017

OTHER PUBLICATIONS

Thermofisher Catalog # 12-9487-42 Data sheet, KLRG1 Monoclonal Antibody (13A2), PE, eBioscience, Retrieved onine from: < URL: https://www.thermofisher.com/order/genome-database/dataSheetPdf?producttype=antibody&productsubtype=antibody_primary&productId=12-9487-42&version=137, Retrieved on 4/9/211, 2021.*

(Continued)

*Primary Examiner* — Claire Kaufman
(74) *Attorney, Agent, or Firm* — Nutter McClennen & Fish LLP

(57) ABSTRACT

A method of treating a subject can include administering to a subject in need thereof an effective amount of a killer cell lectin-like receptor G1 (KLRG1)/ligand binding agent, thereby disrupting KLRG1 signaling and activating CD8+ cytotoxic T and/or NK cells. A method of treating cancer can include administering to a subject in need thereof an effective amount of a killer cell lectin-like receptor G1 (KLRG1)/

(Continued)

ligand binding agent. The methods can treat various cancers, for example melanoma, lung cancer, pancreatic cancer, glioma, breast cancer, and ovarian cancer.

41 Claims, 24 Drawing Sheets

Specification includes a Sequence Listing.

(51) Int. Cl.
    *C12N 15/113*     (2010.01)
    *A61P 35/04*     (2006.01)
    *A61P 35/00*     (2006.01)
    *A61K 39/00*     (2006.01)
    *C12N 15/85*     (2006.01)
    *A61K 38/00*     (2006.01)

(52) U.S. Cl.
    CPC .......... *A61P 35/04* (2018.01); *C07K 16/2896* (2013.01); *C12N 15/1138* (2013.01); *A61K 38/00* (2013.01); *A61K 2039/505* (2013.01); *A61K 2039/507* (2013.01); *A61K 2039/544* (2013.01); *A61K 2039/545* (2013.01); *C07K 16/2818* (2013.01); *C07K 2317/21* (2013.01); *C07K 2317/24* (2013.01); *C07K 2317/33* (2013.01); *C07K 2317/76* (2013.01); *C07K 2317/92* (2013.01); *C12N 15/85* (2013.01); *C12N 2310/14* (2013.01); *C12N 2310/531* (2013.01)

(56) References Cited

U.S. PATENT DOCUMENTS

| | | |
|---|---|---|
| 2002/0155110 A1 | 10/2002 | Takahashi et al. |
| 2011/0091471 A1 | 4/2011 | Yasutake et al. |
| 2014/0050660 A1 | 2/2014 | Chang et al. |

OTHER PUBLICATIONS

BioLegend, Catalog # 368602 Data sheet, Purified anti-human KLRG1 (MAFA) Antibody, Clone 14C2A07, <URL: https://www.biolegend.com/en-us/global-elements/pdf-popup/purified-anti-human-klrg1-mafa-antibody-12460?filename=Purified%20anti-human%20KLRG1%20MAFA%20Antibody.pdf&pdfgen=true>, Retrieved Apr. 9, 2021, Nov. 23, 2015.*
BioLegend, Catalog # 367703, Data sheet, Purifed anti-human LKRG1 (MAFA) Antibody, Clone SA231A2, <URL: https://www.biolegend.com/en-us/global-elements/pdf-popup/purified-anti-human-klrg1-mafa-antibody-12033?filename=Purified%20anti-human%20KLRG1%20MAFA%20Antibody.pdf&pdfgen=true, Retrieved on Apr. 9, 2021, Oct. 2, 2016.I.*
Wang et al., KLRG1 negatively regulates natural killer cell functions through the Akt pathway in individuals with chronic hepatitis C virus infection, J. Virol. 87(21):11626-11536, Nov. 2013.*
Thimme et al., Increased expression of the NK cell receptor KLRG1 by virus-specific CD8 T cells during persistent antigen stimulation, J. Virol., 79(18):12112-12116, Sep. 2005.*
Jackson et al., Driving CAR T-cells forward, Nat. Rev.13:370-383, Mar. 2016.*
Cancer.Net, What are cancer vaccines?, Retrieved online <URL:https://web.archive.org/web/20140421234631/https://www.cancer.net/navigating-cancer-care/how-cancer-treated/immunotherapy-and-vaccines/what-are-cancer-vaccines, Retrieved on Apr. 13, 2021. Apr. 21, 2014.*
Weidle et al., The intriguing options of multispecific antibody format for treatment of cancer, Canc. Genom. Proteom, 10:1-18, 2013.*
Rappl et al., The CD3-Zeta Chimeric Antigen Receptor Overcomes TCR Hypo-Responsiveness of Human Terminal Late-Stage T Cells. PLoS ONE 7(1): e30713 (pp. 1-10). doi:10.1371/journal.pone.0030713, 2012.*
Zuber et al., Epitope mapping of neutralizing monoclonal antibodies to human interferon-gamma using human-bovine interferon-gamma chimeras, J. Interferon Cytokine Res. 36(9):542-551, 2016.*
Ito et al., Killer lectin-like receptor G1 binds three members of the classical cadherin family to inhibit NK cell cytotosicity, J. Exp. Med. 203(2):289-295, Feb. 20, 2006.*
Akbar et al., "Are senescene and exhaustion intertwined or inrelated processes that compromise immunity?", Nature Reviews Immunology, vol. 11, pp. 289-295, Mar. 25, 2011.
Apetoh et al., "Consensus nomenclature for CD8+ T cell phenotypes in cancer.", OncoImmunology, vol. 4, Issue 4, e998538, 2015.
Attig et al., "Simultaneous infiltration of polyfunctional effector and suppressor T cells into renal cell carcinomas.", Cancer Research, vol. 69, Issue 21, pp. 8412-8419, Nov. 2009.
Blackbum et al., "Coregulation of CD8+ T cell exhaustion by multiple inhibitory receptors during chronic viral infection." Nature Immunology, vol. 10, pp. 29-37, 2009.
Brown et al., "RNA interference in mammalian cell culture: design, execution, and analysis of the siRNA effect ", Ambion Technotes, vol. 9, Issue 1, pp. 3-5, 2002.
Brunner et al., "Tumor-infiltrating, interieukin-33-producing effector-memory CD8+ T cells in resected hepatocellular carcinoma prolong patient survival.", Hepatology, vol. 61, Issue 6, pp. 1957-1967, Jun. 2015.
Cyktor et al., "Killer cell lectin-like receptor G1 deficiency significantly enhances survival after *Mycobacterium tuberculosis* infection.", American Society for Microbiology—Infection and Immunity, vol. 81, Issue 4, pp. 1090-1099, Apr. 2013.
Dimitri et al., "Shared blood and muscle CD8+ T-cell expansions in inclusion body myositis.", Brain: A Journal of Neurology, vol. 129, Issue 4, pp. 986-995, Apr. 2006.
Greenberg, et al., "Abslract IB-301: Inhibition of the co-inhibitory receptor KLRG1 reduces murine 4T1 breast cancer metastasis and MC38 colon cancer primary tumor growth and mortality," Cancer Research, vol. 78, No. 13, pp. 1-2, Jul. 2018 (4 pages).
Grundemann et al., "The NK receptor KLRG1 is dispensable for virus-induced NK and CD8+ T-cell differentiation and Function in vivo.", European Journal of Immunology, vol. 40, Issue 5, pp. 1303-1314, May 2010.
Guthmann et al., "A new member of the C-type lectin family is a modulator of the mast cell secretory response.", International Archives of Allergy and Immunology, vol. 107, No. 1-3, pp. 82-86, 1995.
Henson et al., "KLRG1 signaling induces defective Akt (ser473) phosphorylation and proliferatuve dysfunction of highly differentiated CD8+ T cells.", Blood, vol. 113, pp. 6619-6628, 2009.
Henson et al., "Reversal of functional defects in highly differentiated young and old CD8+ T cells by PDL blockade.", Immunology, vol. 135, Issue 4, pp. 355-363, 2012.
Hofmann et al., "Different inhibitory capacities of human and mouse KLRG1 are linked to distinct disulfide-mediated oligomerizations.", European Journal of Immunology, vol. 42, Issue 9, pp. 2484-2490, Sep. 2012.
International Seach Report and Written Opinion for PCT/US17/35621, dated Sep. 1, 2017 (17 pages).
International Search Report and Written Opinion for PCT/US18/62971, dated May 1, 2019 (11 pages).
Legat et al., "Inhibitory Receptor Expression Depends More Dominantly on Differentiation and Activation than "Exhaustion" of Human CD8+ T Cells.", Frontiers in Immunology, vol. 4, No. 455, Dec. 2013.
Li et al., "Structure of natural killer cell receptor KLRG1 bound to E-cadherin reveals basis for MHC-independent missing self recognition.", Immunity, vol. 31, Issue 1, pp. 35-46, 2009.
Mahoney et al., "Combination cancer immunotherapy and new immunomodulatory targets.", Nature Reviews Drug Discovery, vol. 14, pp. 561-584, 2015.
Marcolino et al., "Frequent expression of the natural killer cell receptor KLRG1 in human cord blood T cells: correlation with

(56) References Cited

OTHER PUBLICATIONS replicative history.", The European Journal of Immunology, vol. 34, Issue 10, pp. 2672-2680, Oct. 2004.

Melis et al., "Senescence marker killer cell lectin-like receptor G1 (KLRG1) contributes to TNF-alpha production by nteraction with its soluble E-cadherin ligand in chronically inflamed joints.", Annals of the Rheumatic Disease, vol. 73, Issue 6, pp. 1223-1231, 2014.

Muntzing et al., "Inclusion body myositis: clonal expansions of muscle-infiltrating T cells persist over time.", Scandinavian Journal of Immunology, vol. 58, Issue 2, pp. 195-200, Aug. 2003.

Nishimura et al., "Development of lupus-like autoimmune diseases by disruption of the PD-1 gene encoding an ITIM motif-carrying immunoreceptor ", Immunity, vol. 11, Issue 2, pp. 141-151, Aug. 1, 1999.

Shi et al., "KLRG1 impairs CD4+ T cell responses via p16ink4a and p27kip1 pathways: role in hepatitis B vaccine failure in individuals with hepatitis C virus infection.", The Journal of Immunology, vol. 192, Issue 2, pp. 649-657, 2013.

Tessmer et al., "KLRG1 bind cadherins and preferentially associates with SHIP-1.", International Immunology, vol. 19, Bsue 4, pp. 391-400, Apr. 2007.

Tivol et al., "Loss of CTLA-4 leads to massive lymphoproliferation and fatal multiorgan tissue destruction, revealing a critical negative regulatory role of CTLA-4.", Immunity, vol. 3, Issue 5, pp. 541-547, Nov. 1995.

Voehringer et al., "Lack of proliferative capacity of human effector and memory T cells expressing killer cell lectinlike receptor G1 (KLRG1).", Blood, vol. 100, Issue 10, pp. 3698-3702, 2002.

Brouxhon et al., "Monoclonal Antibody against the Ectodomain of E-Cadherin (DECMA-1) Suppresses Breast Carcinogenesis: Involvement of the HER/PI3K/Akt/mTOR and IAP Pathaways", Clinical Cancer Research, vol. 19, No. 12, Jun. 15, 2013, pp. 3234-3246.

Extended European Search Report for Application No. 17807546.1; dated Jan. 27, 2020 (6 pages).

Jones et al., "N-cadherin upregulation and function in response of smooth muscle cells to arterial injury", Arterioscleroisis, Thrombosis, and Vascular Biology, Highwire Press, Philadelphia, PA, US, vol. 22, No. 12, Dec. 1, 2002, pp. 1972-1977.

* cited by examiner

FIG. 3

| Company/Target | Inhibitory Receptors ||||||||||||
| | CTLA-4 | PD-1 | PD-L1 | TIM-3 | LAG-3 | TIGIT | CeaCAM1 | NKG2A | CD160 | KLRG1 | 2B4 | BTLA |
| --- | --- | --- | --- | --- | --- | --- | --- | --- | --- | --- | --- | --- |
| AZ/Medimmune | ▨ | | ▨ | | | | | | | | | |
| BMS | ▨ | ▨ | | ▨ | ▨ | ▨ | | | | | | |
| Merck | | ▨ | | | | | ▨ | | | | | |
| Agenus | ▨ | | | ▨ | ▨ | | | | | | | |
| Novartis | | ▨ | | | ▨ | | | | | | | |
| Roche | | | | | | | | | | | | |
| Enumeral | | | | ▨ | ▨ | | | | | | | |
| Tesaro | | | | ▨ | ▨ | | | | | | | |
| Medivation | | ▨ | | | | | | | | | | |
| Pfizer | | | | | | | | | | | | |
| J&J | | | | | | | | | | | | |
| Genentech | | | | | | ▨ | | | | | | |
| Xoma | | | | | | | | | | | | |
| AgonOx | | | | | | | | | | | | |
| InnateRharma | | | | | | | | ▨ | | | | |
| TG Therapeutics | | | ▨ | | | | | | | | | |
| CellDex | | | | | | | | | | | | |
| Seattle Genetics | | | | | | | | | | | | |
| Checkpoint Ther | | | ▨ | | | | | | | | | |
| OncoMed | | | | | | ▨ | | | | | | |
| FivePrime | | | | | | | | | | | | |
| LeapTx | | | | | | | | | | | | |
| Elsalys | | | | | | | | | ▨ | | | |

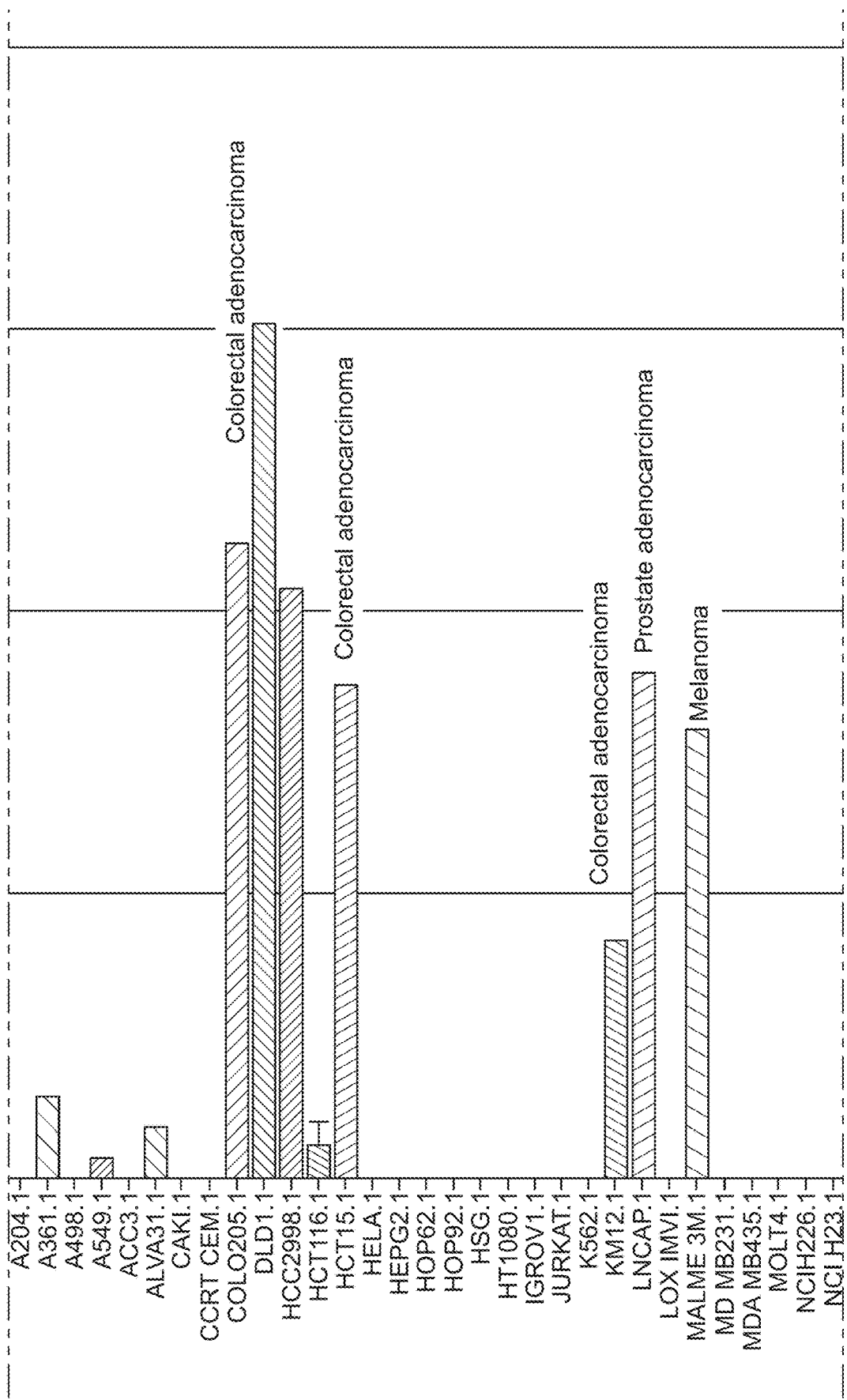

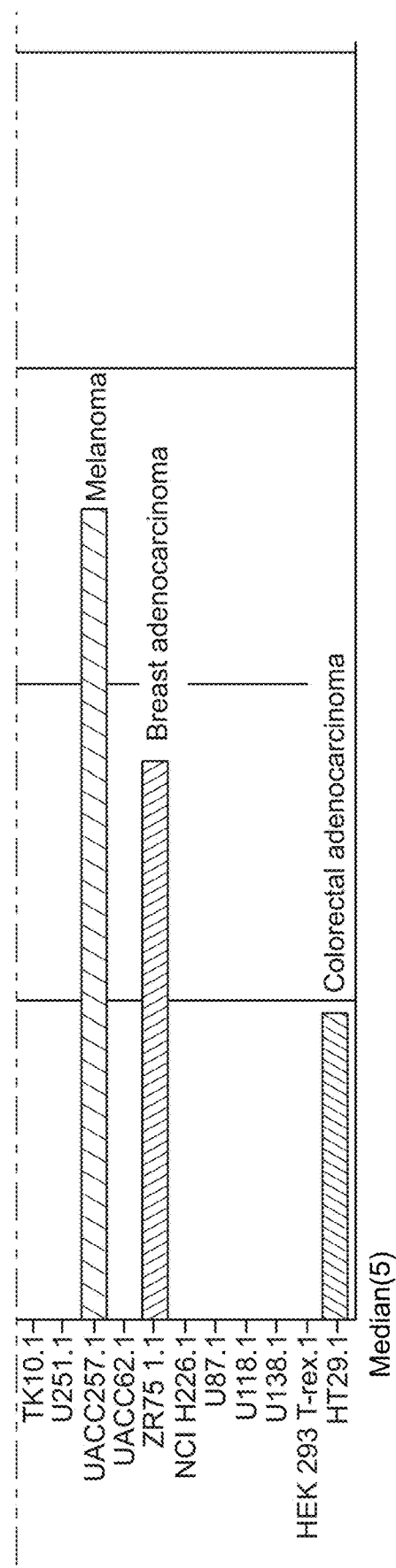

SEQUENCE LISTING

```
<160> NUMBER OF SEQ ID NOS: 7

<210> SEQ ID NO 1
<211> LENGTH: 135
<212> TYPE: PRT
<213> ORGANISM: Human

<400> SEQUENCE: 1

Cys Gln Gly Ser Asn Tyr Ser Thr Cys Ala Ser Cys Pro Ser Cys Pro
1               5                   10                  15

Asp Arg Trp Met Lys Tyr Gly Asn His Cys Tyr Tyr Phe Ser Val Glu
            20                  25                  30

Glu Lys Asp Trp Asn Ser Ser Leu Glu Phe Cys Leu Ala Arg Asp Ser
        35                  40                  45

His Leu Leu Val Ile Thr Asp Asn Gln Glu Met Ser Leu Leu Gln Val
    50                  55                  60

Phe Leu Ser Glu Ala Phe Cys Trp Ile Gly Leu Arg Asn Asn Ser Gly
65                  70                  75                  80

Trp Arg Trp Glu Asp Gly Ser Pro Leu Asn Phe Ser Arg Ile Ser Ser
                85                  90                  95

Asn Ser Phe Val Gln Thr Cys Gly Ala Ile Asn Lys Asn Gly Leu Gln
            100                 105                 110

Ala Ser Ser Cys Glu Val Pro Leu His Trp Val Cys Lys Lys Cys Pro
        115                 120                 125

Phe Ala Asp Gln Ala Leu Phe
    130                 135

<210> SEQ ID NO 2
<211> LENGTH: 129
<212> TYPE: PRT
<213> ORGANISM: Human

<400> SEQUENCE: 2

Cys Gln Gly Ser Asn Tyr Ser Thr Cys Ala Ser Cys Pro Ser Cys Pro
1               5                   10                  15

Asp Arg Trp Met Lys Tyr Gly Asn His Cys Tyr Tyr Phe Ser Val Glu
            20                  25                  30

Glu Lys Asp Trp Asn Ser Ser Leu Glu Phe Cys Leu Ala Arg Asp Ser
        35                  40                  45

His Leu Leu Val Ile Thr Asp Asn Gln Glu Met Ser Leu Leu Gln Val
    50                  55                  60

Phe Leu Ser Glu Ala Phe Cys Trp Ile Gly Leu Arg Asn Asn Ser Gly
65                  70                  75                  80

Trp Arg Trp Glu Asp Gly Ser Pro Leu Asn Phe Ser Arg Ile Ser Ser
                85                  90                  95

Asn Ser Phe Val Gln Thr Cys Gly Ala Ile Asn Lys Asn Gly Leu Gln
```

```
                100             105             110
Ala Ser Ser Cys Glu Val Pro Leu His Trp Val Cys Lys Lys Val Arg
        115             120             125

Leu

<210> SEQ ID NO 3
<211> LENGTH: 129
<212> TYPE: PRT
<213> ORGANISM: Cynomolgus

<400> SEQUENCE: 3

Cys Gln Gly Ser Lys Tyr Ser Thr Cys Ala Ser Cys Pro Ser Cys Pro
1               5                   10                  15

Asp His Trp Met Lys Tyr Gly Asn His Cys Tyr Tyr Phe Ser Val Glu
            20                  25                  30

Lys Lys Asp Trp Ile Ser Ser Leu Glu Phe Cys Leu Ala Arg Asp Ser
        35                  40                  45

His Leu Leu Met Ile Thr Asp Lys Gln Glu Met Ser Leu Leu Gln Asp
    50                  55                  60

Phe Leu Ser Glu Ala Phe His Trp Val Gly Leu Arg Asn Asn Ser Gly
65                  70                  75                  80

Trp Arg Trp Glu Asp Gly Ser Pro Leu Asn Phe Ser Arg Ile Tyr Ser
                85                  90                  95

Asn Ser Leu Val Gln Thr Cys Gly Ala Ile Asn Lys Asn Ser Leu Gln
            100                 105                 110

Ala Ser Ser Cys Glu Val Ser Leu Gln Trp Val Cys Lys Lys Val Arg
        115                 120                 125

Leu

<210> SEQ ID NO 4
<211> LENGTH: 882
<212> TYPE: PRT
<213> ORGANISM: Human

<400> SEQUENCE: 4

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His His Arg Pro Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160
```

```
Ile Ser Cys Pro Glu Asn Glu Lys Gly Pro Phe Pro Lys Asn Leu Val
            165                 170                 175

Gln Ile Lys Ser Asn Lys Asp Lys Glu Gly Lys Val Phe Tyr Ser Ile
        180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
        290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
    370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
        435                 440                 445

Gln Tyr Ile Leu His Val Ala Val Thr Asn Val Val Pro Phe Glu Val
        450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
        515                 520                 525

Thr Ala Asn Trp Leu Glu Ile Asn Pro Asp Thr Gly Ala Ile Ser Thr
        530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
```

```
            580                 585                 590
Pro Ile Pro Glu Pro Arg Thr Ile Phe Phe Cys Glu Arg Asn Pro Lys
            595                 600                 605

Pro Gln Val Ile Asn Ile Ile Asp Ala Asp Leu Pro Pro Asn Thr Ser
        610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
            645                 650                 655

Ala Leu Glu Val Gly Asp Tyr Lys Ile Asn Leu Lys Leu Met Asp Asn
        660                 665                 670

Gln Asn Lys Asp Gln Val Thr Thr Leu Glu Val Ser Val Cys Asp Cys
    675                 680                 685

Glu Gly Ala Ala Gly Val Cys Arg Lys Ala Gln Pro Val Glu Ala Gly
        690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Gly Glu Glu Asp Gln Asp Phe Asp
        755                 760                 765

Leu Ser Gln Leu His Arg Gly Leu Asp Ala Arg Pro Glu Val Thr Arg
770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
            805                 810                 815

Ala Ala Asp Thr Asp Pro Thr Ala Pro Pro Tyr Asp Ser Leu Leu Val
        820                 825                 830

Phe Asp Tyr Glu Gly Ser Gly Ser Glu Ala Ala Ser Leu Ser Ser Leu
        835                 840                 845

Asn Ser Ser Glu Ser Asp Lys Asp Gln Asp Tyr Asp Tyr Leu Asn Glu
        850                 855                 860

Trp Gly Asn Arg Phe Lys Lys Leu Ala Asp Met Tyr Gly Gly Gly Glu
865                 870                 875                 880

Asp Asp

<210> SEQ ID NO 5
<211> LENGTH: 906
<212> TYPE: PRT
<213> ORGANISM: Human

<400> SEQUENCE: 5

Met Cys Arg Ile Ala Gly Ala Leu Arg Thr Leu Leu Pro Leu Leu Ala
1               5                   10                  15

Ala Leu Leu Gln Ala Ser Val Glu Ala Ser Gly Glu Ile Ala Leu Cys
            20                  25                  30

Lys Thr Gly Phe Pro Glu Asp Val Tyr Ser Ala Val Leu Ser Lys Asp
        35                  40                  45

Val His Glu Gly Gln Pro Leu Leu Asn Val Lys Phe Ser Asn Cys Asn
    50                  55                  60

Gly Lys Arg Lys Val Gln Tyr Glu Ser Ser Glu Pro Ala Asp Phe Lys
```

```
            65                  70                  75                  80
Val Asp Glu Asp Gly Met Val Tyr Ala Val Arg Ser Phe Pro Leu Ser
                    85                  90                  95

Ser Glu His Ala Lys Phe Leu Ile Tyr Ala Gln Asp Lys Glu Thr Gln
                100                 105                 110

Glu Lys Trp Gln Val Ala Val Lys Leu Ser Leu Lys Pro Thr Leu Thr
            115                 120                 125

Glu Glu Ser Val Lys Glu Ser Ala Glu Val Glu Ile Val Phe Pro
    130                 135                 140

Arg Gln Phe Ser Lys His Ser Gly His Leu Gln Arg Gln Lys Arg Asp
145                 150                 155                 160

Trp Val Ile Pro Pro Ile Asn Leu Pro Glu Asn Ser Arg Gly Pro Phe
                165                 170                 175

Pro Gln Glu Leu Val Arg Ile Arg Ser Asp Arg Asp Lys Asn Leu Ser
                180                 185                 190

Leu Arg Tyr Ser Val Thr Gly Pro Gly Ala Asp Gln Pro Pro Thr Gly
            195                 200                 205

Ile Phe Ile Ile Asn Pro Ile Ser Gly Gln Leu Ser Val Thr Lys Pro
    210                 215                 220

Leu Asp Arg Glu Gln Ile Ala Arg Phe His Leu Arg Ala His Ala Val
225                 230                 235                 240

Asp Ile Asn Gly Asn Gln Val Glu Asn Pro Ile Asp Ile Val Ile Asn
                245                 250                 255

Val Ile Asp Met Asn Asp Asn Arg Pro Glu Phe Leu His Gln Val Trp
                260                 265                 270

Asn Gly Thr Val Pro Glu Gly Ser Lys Pro Gly Thr Tyr Val Met Thr
            275                 280                 285

Val Thr Ala Ile Asp Ala Asp Asp Pro Asn Ala Leu Asn Gly Met Leu
    290                 295                 300

Arg Tyr Arg Ile Val Ser Gln Ala Pro Ser Thr Pro Ser Pro Asn Met
305                 310                 315                 320

Phe Thr Ile Asn Asn Glu Thr Gly Asp Ile Ile Thr Val Ala Ala Gly
                325                 330                 335

Leu Asp Arg Glu Lys Val Gln Gln Tyr Thr Leu Ile Ile Gln Ala Thr
            340                 345                 350

Asp Met Glu Gly Asn Pro Thr Tyr Gly Leu Ser Asn Thr Ala Thr Ala
    355                 360                 365

Val Ile Thr Val Thr Asp Val Asn Asp Asn Pro Pro Glu Phe Thr Ala
    370                 375                 380

Met Thr Phe Tyr Gly Glu Val Pro Glu Asn Arg Val Asp Ile Ile Val
385                 390                 395                 400

Ala Asn Leu Thr Val Thr Asp Lys Asp Gln Pro His Thr Pro Ala Trp
                405                 410                 415

Asn Ala Val Tyr Arg Ile Ser Gly Gly Asp Pro Thr Gly Arg Phe Ala
                420                 425                 430

Ile Gln Thr Asp Pro Asn Ser Asn Asp Gly Leu Val Thr Val Val Lys
            435                 440                 445

Pro Ile Asp Phe Glu Thr Asn Arg Met Phe Val Leu Thr Val Ala Ala
    450                 455                 460

Glu Asn Gln Val Pro Leu Ala Lys Gly Ile Gln His Pro Pro Gln Ser
465                 470                 475                 480

Thr Ala Thr Val Ser Val Thr Val Ile Asp Val Asn Glu Asn Pro Tyr
                485                 490                 495
```

Phe Ala Pro Asn Pro Lys Ile Ile Arg Gln Glu Gly Leu His Ala
            500                 505                 510

Gly Thr Met Leu Thr Thr Phe Thr Ala Gln Asp Pro Asp Arg Tyr Met
        515                 520                 525

Gln Gln Asn Ile Arg Tyr Thr Lys Leu Ser Asp Pro Ala Asn Trp Leu
    530                 535                 540

Lys Ile Asp Pro Val Asn Gly Gln Ile Thr Thr Ile Ala Val Leu Asp
545                 550                 555                 560

Arg Glu Ser Pro Asn Val Lys Asn Asn Ile Tyr Asn Ala Thr Phe Leu
                565                 570                 575

Ala Ser Asp Asn Gly Ile Pro Pro Met Ser Thr Gly Thr Thr Leu Gln
            580                 585                 590

Ile Tyr Leu Leu Asp Ile Asn Asp Asn Ala Pro Gln Val Leu Pro Gln
        595                 600                 605

Glu Ala Glu Thr Cys Glu Thr Pro Asp Pro Asn Ser Ile Asn Ile Thr
    610                 615                 620

Ala Leu Asp Tyr Asp Ile Asp Pro Asn Ala Gly Pro Phe Ala Phe Asp
625                 630                 635                 640

Leu Pro Leu Ser Pro Val Thr Ile Lys Arg Asn Trp Thr Ile Thr Arg
                645                 650                 655

Leu Asn Gly Asp Phe Ala Gln Leu Asn Leu Lys Ile Lys Phe Leu Glu
            660                 665                 670

Ala Gly Ile Tyr Glu Val Pro Ile Ile Thr Asp Ser Gly Asn Pro
        675                 680                 685

Pro Lys Ser Asn Ile Ser Ile Leu Arg Val Lys Val Cys Gln Cys Asp
    690                 695                 700

Ser Asn Gly Asp Cys Thr Asp Val Asp Arg Ile Val Gly Ala Gly Leu
705                 710                 715                 720

Gly Thr Gly Ala Ile Ile Ala Ile Leu Cys Ile Ile Ile Leu Leu
                725                 730                 735

Ile Leu Val Leu Met Phe Val Val Trp Met Lys Arg Arg Asp Lys Glu
            740                 745                 750

Arg Gln Ala Lys Gln Leu Leu Ile Asp Pro Glu Asp Asp Val Arg Asp
        755                 760                 765

Asn Ile Leu Lys Tyr Asp Glu Glu Gly Gly Gly Glu Glu Asp Gln Asp
    770                 775                 780

Tyr Asp Leu Ser Gln Leu Gln Gln Pro Asp Thr Val Glu Pro Asp Ala
785                 790                 795                 800

Ile Lys Pro Val Gly Ile Arg Arg Met Asp Glu Arg Pro Ile His Ala
                805                 810                 815

Glu Pro Gln Tyr Pro Val Arg Ser Ala Ala Pro His Pro Gly Asp Ile
            820                 825                 830

Gly Asp Phe Ile Asn Glu Gly Leu Lys Ala Ala Asp Asn Asp Pro Thr
        835                 840                 845

Ala Pro Pro Tyr Asp Ser Leu Leu Val Phe Asp Tyr Glu Gly Ser Gly
    850                 855                 860

Ser Thr Ala Gly Ser Leu Ser Ser Leu Asn Ser Ser Ser Ser Gly Gly
865                 870                 875                 880

Glu Gln Asp Tyr Asp Tyr Leu Asn Asp Trp Gly Pro Arg Phe Lys Lys
                885                 890                 895

Leu Ala Asp Met Tyr Gly Gly Gly Asp Asp
            900                 905

```
<210> SEQ ID NO 6

<400> SEQUENCE: 6

000

<210> SEQ ID NO 7
<211> LENGTH: 570
<212> TYPE: RNA
<213> ORGANISM: Human

<400> SEQUENCE: 7
augacugaca  guguuauuua  uuccauguua  gaguugccua  cggcaaccca  agcccagaau      60
gacuacggac  cacagcaaaa  aucuuccucu  uccaagccuu  cuuguucuug  ccuuguggca     120
auaacuuugg  ggcuucugac  ugcaguucuu  cugagugugc  ugcuauacca  guggauccug     180
ugccagggcu  ccaacuacuc  cacuugugcc  agcuguccua  gcugcccaga  ccgcuggaug     240
aaauauggua  accauuguua  uuauuucuca  guggaggaaa  aggacuggaa  uucuagucug     300
gaauucugcc  uagccagaga  cucacaccuc  cuugugauaa  cggacaauca  ggaaaugagc     360
cugcuccaag  uuuuccucag  ugaggccuuu  ugcuggauug  gucugaggaa  caauucggc      420 uggagguggg  aagacggauc  accucuaaac  uucucaagga  uuucuucuaa  uagcuuugug     480
cagacaugcg  gugccaucaa  caaaaauggu  cuucaagccu  caagcuguga  aguuccuuua     540
cacggggugu  guaagaaggu  cagacuuuga                                         570
```

KLRG1 ANTAGONIST SIGNALING THERAPY

FIELD OF THE INVENTION

The present invention generally relates to KLRG1 signaling therapy and, in various embodiments, more specifically to KLRG1-based cancer therapy.

SEQUENCE LISTING

This application contains a Sequence Listing which has been submitted electronically in ASCII format and is hereby incorporated by reference in its entirety. Said ASCII copy, created on Nov. 30, 2018, is named 117307-0007_Sequence-_Listing.txt and is 19,630 bytes in size.

BACKGROUND

Expression of immune checkpoint signaling molecules on immune cells is important to immune system regulation. Co-expression of checkpoint molecules can occur on T cells as well as cancer cells. Prolonged exposure of T cells to cancer cells and to dendritic cells that have processed cancer antigens can lead to complete or partial loss of their immune effector function, resulting in immune exhaustion. Accordingly, inhibition of checkpoint molecules, such as CTLA-4 and PD-1, can re-activate the immune system and lead to effective tumor treatment. Numerous checkpoint signaling molecules expressed on T cells as well as other immune cells have been identified. However, therapeutic developments based upon these signaling molecules are limited and there remains a need for new therapeutics utilizing immune checkpoint signaling pathways for medical therapy.

SUMMARY OF THE INVENTION

The invention is based, at least in part, on the discovery that killer cell lectin-like receptor G1 (KLRG1) can function as a co-inhibitory receptor like a number of other T cell co-inhibitory receptors such as CTLA-4, PD-1, LAG-3, and TIM-3. Unlike in mice and the teachings of many preceding studies, in humans KLRG1 is a favorable target for immunotherapy such as cancer immunotherapy. For example, administering to a subject in need thereof an effective amount of killer cell lectin-like receptor G1 (KLRG1)/ligand binding agent can disrupt KLRG1 signaling and activate CD8$^+$ cytotoxic T and/or NK cells. Thus, the invention has numerous therapeutic uses. For example, the invention can be used for treating cancer through the administration of an effective amount of a killer cell lectin-like receptor G1 (KLRG1)/ligand binding agent.

Advantages of the invention include the ability to preferentially target CD8$^+$ cytotoxic T and/or NK cells. Advantages of the invention include greater efficacy and reduced side effects. For example, the population of KLRG1 expressing immune cells more abundantly expresses cytotoxic molecules than the population of CTLA-4 or PD-1 expressing immune cells, hence the potential for greater efficacy; and KLRG1 is a marker that increases with antigen expression, predicting more specific antigen directed immune responses and, hence the potential for reduced side effects.

In various aspects and embodiments, the invention provides methods of treatment comprising administering to a subject in need thereof an effective amount of a killer cell lectin-like receptor G1 (KLRG1)/ligand binding agent, thereby disrupting KLRG1 signaling and activating CD8$^+$ cytotoxic T and/or NK cells.

In various aspects and embodiments, the invention provides a method of treating cancer comprising administering to a subject in need thereof an effective amount of a killer cell lectin-like receptor G1 (KLRG1)/ligand binding agent.

In various aspects and embodiments, the invention provides a killer cell lectin-like receptor G1 (KLRG1) antagonist comprising (i) a killer cell lectin-like receptor G1 (KLRG1)/ligand binding agent or (ii) an RNAi agent that suppresses KLRG1 expression.

In various aspects and embodiments, the invention provides an mRNA or cDNA encoding the KLRG1 antagonist according to the invention.

In various aspects and embodiments, the invention provides a killer cell lectin-like receptor G1 (KLRG1)/ligand binding agent that neutralizes KLRG1/cadherin (e.g., E-cadherin) binding and disrupts KLRG1 signaling, thereby activating CD8$^+$ cytotoxic T and/or NK cells. The binding agent can cross compete with at least one of clone 13F12F2, 14C2A07, SA231A2, 2F1, 13A2, or REA261. The binding agent can be a human or humanized monoclonal antibody, or a binding fragment thereof, or antibody mimetic.

In various aspects and embodiments, the invention provides a method of treating a subject comprising administering to a subject in need thereof an effective amount of KLRG1 antagonist, thereby disrupting KLRG1 signaling and activating CD8$^+$ cytotoxic T and/or NK cells.

In various aspects and embodiments, the invention provides a method of treating cancer comprising administering to a subject in need thereof an effective amount of KLRG1 antagonist.

The invention provides a method of treating a melanoma comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating CD8$^+$ cytotoxic T and/or NK cells.

The invention provides a method of treating a lung cancer comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating CD8$^+$ cytotoxic T and/or NK cells.

The invention provides a method of treating a pancreatic cancer comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating CD8$^+$ cytotoxic T and/or NK cells.

The invention provides a method of treating a glioma comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating CD8+ cytotoxic T and/or NK cells.

The invention provides a method of treating a breast cancer comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating CD8+ cytotoxic T and/or NK cells.

The invention provides a method of treating an ovarian cancer comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating CD8+ cytotoxic T and/or NK cells.

In various embodiments, the subject is a mammal, such as a human.

In various embodiments, methods according to the invention are carried out in vivo (e.g., as opposed to ex vivo).

In various embodiments, the binding agent is an antibody or antigen binding fragment thereof, or antibody mimetic.

In various embodiments, the antibody or antigen binding fragment thereof, or antibody mimetic comprises a human or humanized antibody.

In various embodiments, the antibody or antigen binding fragment thereof, or antibody mimetic comprises:
  a. a full length antibody Fab portion that binds KLRG1;
  b. a full length antibody Fab portion that binds E-cadherin;
  c. a full length antibody Fab portion that binds N-cadherin;
  d. a full length antibody Fab portion that binds R-cadherin;
  e. a fusion protein E-cadherin/Fc;
  f. a fusion protein R-cadherin/Fc;
  g. a fusion protein N-cadherin/Fc;
  h. a chimeric antigen receptor; or
  i. a multispecific antibody.

In various embodiments, the binding agent is a chimeric antigen receptor and the chimeric antigen receptor comprises a specificity portion of a KLRG1 antibody grafted onto a T cell.

In various embodiments, the binding agent is a multispecific antibody. The multispecific antibody can comprise a bispecific or trispecific antibody.

In various embodiments, the binding agent binds KLRG1.

In various embodiments, the KLRG1 is the extracellular domain of human KLRG1.

In various embodiments, the binding agent binds a KLRG1 ligand.

In various embodiments, the KLRG1 ligand is human E-cadherin, N-cadherin, or R-cadherin.

In various embodiments, the binding agent binds KLRG1 and/or cadherin at a KLRG1/cadherin binding site.

In various embodiments, the subject has an epithelial cancer.

In various embodiments, the subject has a carcinoma.

In various embodiments, the subject has a uveal melanoma, uterine carcinoma, uterine carcinosarcoma, thyroid carcinoma, thymoma, testicular germ cell tumor, melanoma, sarcoma, rectal adenocarcinoma, prostate cancer, pheochromocytoma, pancreatic adenocarcinoma, ovarian cystadenocarcinoma, mesothelioma, lung squamous cell carcinoma, lung adenocarcinoma, liver hepatocellular carcinoma, kidney papillary cell carcinoma, kidney clear cell carcinoma, kidney chromophobe carcinoma, head and neck squamous cell carcinoma, glioblastoma multiforme, diffuse large B-cell lymphoma, colon adenocarcinoma, cholangiocarcinoma, cervical and/or endocervical cancer, breast invasive carcinoma, brain low grade glioma, bladder cancer, or acute myeloid leukemia.

In various embodiments, the subject has a melanoma.

In various embodiments, the subject has a lung cancer.

In various embodiments, the subject has a pancreatic cancer.

In various embodiments, the subject has a glioma.

In various embodiments, the subject has a breast cancer.

In various embodiments, the subject has an ovarian cancer.

In various embodiments, the methods further comprise administering to the subject an effective amount of a checkpoint modulator therapy.

In various embodiments, the KLRG1/ligand binding agent and checkpoint modulator therapy are synergistic.

In various embodiments, the method further comprises administering to the subject an effective amount of a cancer vaccine therapy.

In various embodiments, the KLRG1/ligand binding agent and cancer vaccine therapy are synergistic.

In various embodiments, the invention can use a combination of the KLRG1/ligand binding agent and one or more additional Active Pharmaceutical Ingredient (API). In some embodiments, the API may be a polynucleotide (including an oligonucleotide) a protein or a small molecule. An API can include, for example, an anticancer agent, an antibiotic agent, an antiviral agent, an anti-fungal agent, or an analgesic.

In various embodiments, the method further comprises administering to the subject an effective amount of a cancer chemotherapy.

In various embodiments, the checkpoint modulator therapy comprises an anti-PD-1, anti-PD-L1, or anti-CTLA-4 therapy.

In various embodiments, the subject has failed or has not responded to a prior cancer therapy.

In various embodiments, the subject has elevated KLRG1 expression. The elevated KLRG1 expression can comprise elevated KLRG1 expression on CD8+ cytotoxic T and/or NK cells. In various embodiments, the method can further comprise testing the subject for elevated KLRG1 expression (e.g., before beginning and/or during the therapy).

In various embodiments, the subject has elevated cadherin expression (e.g., E-cadherin). The elevated cadherin expression can comprise elevated cadherin expression on cancer cells. In various embodiments, the method can further comprise testing the subject for elevated cadherin expression (e.g., before beginning and/or during the therapy).

In various embodiments, the treatment can prolong the subject's survival. In various embodiments, the treatment can prevent or reduce the progression or the cancer and/or metastasis.

In various embodiments, the binding agent is administered by providing an mRNA encoding the binding agent to the subject.

In various embodiments, the antagonist disrupts KLRG1 signaling, thereby activating CD8+ cytotoxic T and/or NK cells.

In various embodiments, the antagonist binds the extracellular domain of human KLRG1 or binds a KLRG1 ligand.

In various embodiments, the KLRG1 antagonist comprises an antibody or antigen binding fragment.

In various embodiments, the KLRG1 antagonist comprises an Fc-cadherin fusion protein.

In various embodiments, the antibody is monoclonal.

In various embodiments, the antibody is human or humanized.

In various embodiments, the KLRG1 antagonist comprises a binding agent that blocks or competes with KLRG1-ligand binding.

In various embodiments, the KLRG1 antagonist comprises a binding agent that cross reacts with the extracellular domains of human and cynomolgus KLRG1, or the human and cynomolgus KLRG1 ligand.

In various embodiments, the KLRG1 antagonist comprises a binding agent that binds to an epitope of (i) the extracellular domain of KLRG1 or (ii) the KLRG1 ligand, wherein the epitope is at least 90% identical in human and cynomolgus. In one embodiment, the KLRG1 antagonist comprises a binding agent that binds to the same epitope as any one of clone 13F12F2, 14C2A07, SA231A2, 2F1, 13A2, or REA261.

In various embodiments, the KLRG1 antagonist comprises a binding agent that binds to KLRG1 and that is not clone 13F12F2, 14C2A07, SA231A2, 2F1, 13A2, or REA261 (or another previously described anti-KLRG1 antibody).

In various embodiments, the KLRG1 antagonist comprises a binding agent that binds to KLRG1 and that is not a mouse antibody.

In various embodiments, the antagonist or binding agent cross competes with at least one of clone 13F12F2, 14C2A07, SA231A2, 2F1, 13A2, or REA261.

In various embodiments, the antagonist, e.g., binding agent, neutralizes KLRG1/E-cadherin binding.

In various embodiments, the binding agent is a human or humanized monoclonal antibody, or binding fragment thereof, or antibody mimetic.

In various embodiments, the KLRG1 antagonist comprises an RNAi agent. The RNAi agent can be, inter alia, an siRNA or an mRNA.

These and other advantages of the present technology will be apparent when reference is made to the accompanying drawings and the following description.

BRIEF DESCRIPTION OF THE DRAWINGS

FIG. 3 shows a summary of published drug development programs for co-inhibitory receptor modulation by various pharmaceutical companies.

FIG. 17A shows a comparison of proportions of infiltrating CD8$^+$ T cells that express either KLRG1 or PD-1. FIG. 17B shows the proportion of PD-1 negative CD8$^+$ T cells that express KLRG1. FIG. 17C shows the proportion of PD-1 negative CD8$^+$ T cells that express KLRG1, organized by each of 17 melanoma patient samples (e.g., P53 is patient 53 from dataset GSE72056 within GEO database). FIG. 17D shows individual CD8$^+$ T cell expression levels of KLRG1 (log 2 transcripts per million) organized by each patient sample.

FIG. 18A shows single cell RNA-seq analysis of expression of KLRG1 and PD-1 ligands in 1184 patient biopsy melanoma cells shows markedly greater E-cadherin and N-cadherin expression than PD-L1 and PD-L2. Mean and SEM shown. FIG. 18B shows fourteen melanoma patient samples show a mean of 76% of melanoma cells expressing E-cadherin or N-cadherin compared to 11% expressing PD-L1 or PD-L2. FIGS. 18C and 18D show individual melanoma cell (1184 cells) expression levels (log 2 transcripts per million, "TPM") of E-cadherin (FIG. 18C) organized by each patient sample greatly exceed those of PD-L1 (FIG. 18D).

Figure 1:
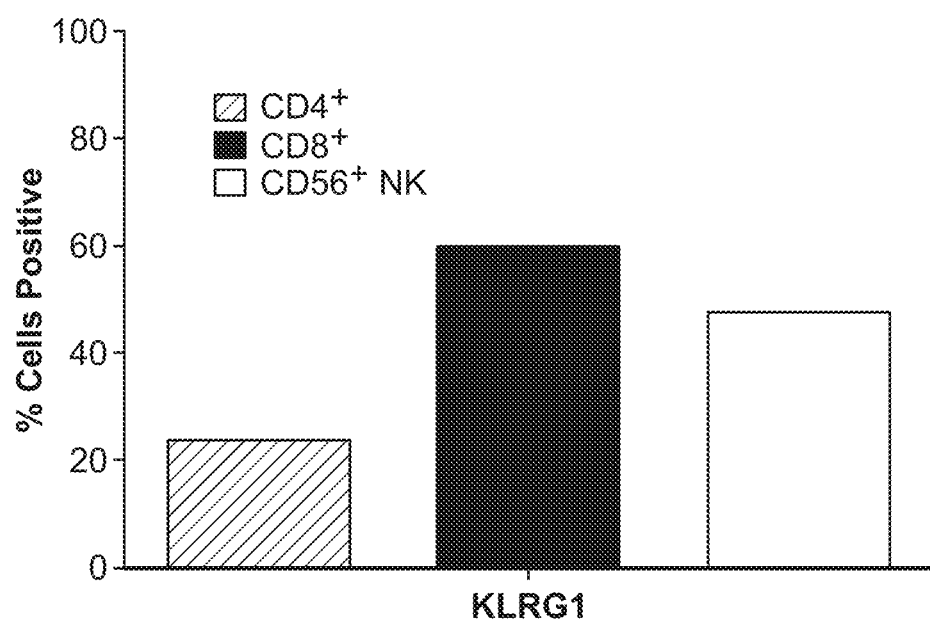
FIG. 1 shows human KLRG1 is expressed on greater proportions of cytotoxic T and NK cells than helper T cells.

While the invention comprises embodiments in many different forms, there are shown in the drawings and will herein be described in detail several specific embodiments with the understanding that the present disclosure is to be considered as an exemplification of the principles of the technology and is not intended to limit the invention to the embodiments illustrated.

BRIEF DESCRIPTION OF THE SEQUENCES

SEQ ID NO:1 is the sequence of human KLRG1 ECD isotype 1.
SEQ ID NO:2 is the sequence of human KLRG1 ECD isotype 2.
SEQ ID NO:3 is the sequence of cynomolgus KLRG1 ECD.
SEQ ID NO:4 is the sequence of human E-cadherin.
SEQ ID NO:5 is the sequence of human N-cadherin.
SEQ ID NO:6 is the sequence of human R-cadherin.
SEQ ID NO:7 is the sequence of human KLRG1 mRNA.

DETAILED DESCRIPTION

The invention is based, at least in part, on the discovery that KLRG1 can function as a co-inhibitory receptor like a number of other T cell co-inhibitory receptors such as CTLA-4, PD-1, LAG-3, and TIM-3. Unlike in mice and the teachings of many preceding studies, in humans KLRG1 is a favorable target for immunotherapy (e.g., cancer immunotherapy). For example, administering to a subject in need thereof an effective amount of a killer cell lectin-like receptor G1 (KLRG1)/ligand binding agent can disrupt KLRG1 signaling and activate $CD8^+$ cytotoxic T and/or NK cells. Thus, the invention has numerous therapeutic uses. For example, the invention can be used for treating cancer through the administration of an effective amount of a killer cell lectin-like receptor G1 (KLRG1)/ligand binding agent.

Advantages of the invention include the ability to preferentially target $CD8^+$ cytotoxic T and/or NK cells. Advantages of the invention include greater efficacy and reduced side effects. For example, the population of KLRG1 expressing immune cells more abundantly express cytotoxic molecules than the population of CTLA-4 or PD-1 expressing immune cells, hence potential for greater efficacy; and KLRG1 is a marker that increases with antigen experience, predicting more specific antigen directed immune responses and, hence potential for reduced side effects.

Accordingly, in various aspects and embodiments, the invention provides methods of treating a subject comprising administering to a subject in need thereof an effective amount of a killer cell lectin-like receptor G1 (KLRG1)/ligand binding agent, thereby disrupting KLRG1 signaling and activating $CD8^+$ cytotoxic T and/or NK cells. The invention also provides methods of treating cancer comprising administering to a subject in need thereof an effective amount of a killer cell lectin-like receptor G1 (KLRG1)/ligand binding agent.

In various aspects and embodiments, the invention provides a killer cell lectin-like receptor G1 (KLRG1) antagonist comprising (i) a killer cell lectin-like receptor G1 (KLRG1)/ligand binding agent or (ii) an RNAi agent that suppresses KLRG1 expression. The invention also provides an mRNA or cDNA encoding the KLRG1 antagonist according to the invention. The invention also provides a method of treating a subject comprising administering to a subject in need thereof an effective amount of KLRG1 antagonist, thereby disrupting KLRG1 signaling and activating $CD8^+$ cytotoxic T and/or NK cells. The invention also provides a method of treating cancer comprising administering to a subject in need thereof an effective amount of KLRG1 antagonist.

The various features of the invention such as KLRG1 and its ligands, binding agents, combination therapies, treatment and administration, cancers, and illustrative examples are discussed, in turn, below.

Killer Cell Lectin-Like Receptor G1 (KLRG1) and its Ligands

Killer cell lectin-like receptor G1 (KLRG1) is type II transmembrane protein surface co-inhibitory receptor modulating the activity of T and NK cells. Its extracellular portion contains a C-type lectin domain whose known ligands are cadherins and its intracellular portion contains an immunoreceptor tyrosine-based inhibitory motif (ITIM) domain responsible for co-inhibition of T cell receptor (TCR) mediated signaling (Tessmer et al., 2007). In various embodiments, the ligand can be E-cadherin, N-cadherin, R-cadherin, or a combination thereof.

KLRG1 distribution and function differ in the rodent compared to the human. Originally identified on a rodent mast cell line (Guthmann et al., 1995), KLRG1 is not expressed on human mast cells, basophils, monocytes, or neutrophils (Voehringer et al., 2002). Human KLRG1 is a more potent co-inhibitory receptor than mouse KLRG1. KLRG1-mediated inhibition under physiological conditions is only observed with human lymphocytes because KLRG1 dimers have greater potency than monomers, and human KLRG1 forms exclusively dimers while mouse KLRG1 exists as monomers and dimers (Hofmann et al., 2012).

Figures 2A, 2B:
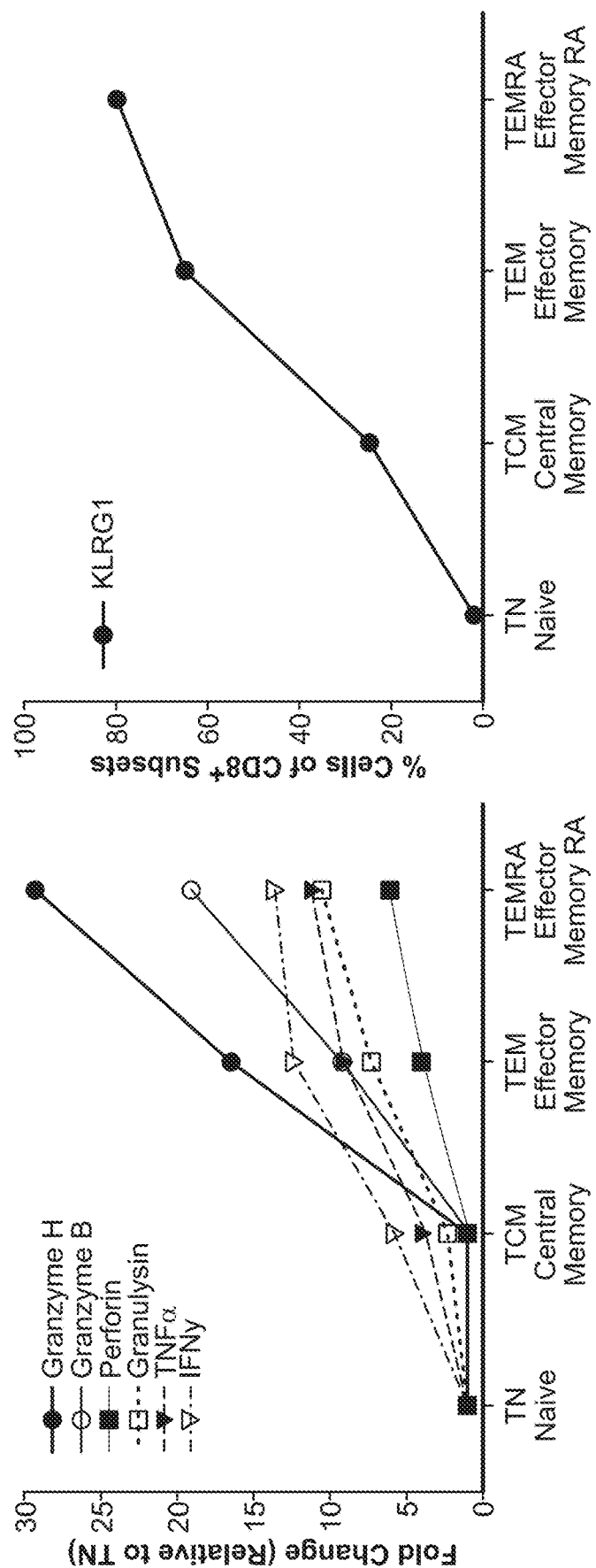
FIGS. 2A and 2B show a progression of increasing expression of KLRG1 on T cells with increased differentiation.

KLRG1 expression in humans is limited to T and NK cells. It is expressed on greater proportions of cytotoxic T and NK cells than helper T cells (FIG. 1, KLRG1 expression of lymphocyte subsets, human blood flow cytometry). Specifically, FIG. 1 shows the greater expression of KLRG1 on cytotoxic $CD8^+$ T cells and NK cells than on $CD4^+$ helper T cells. Within the $CD8^+$ cytotoxic T cell population, increased KLRG1 expression correlates with increased antigen specific potency (FIGS. 2A and B). Specifically, FIG. 2 shows increasing expression of KLRG1 on T cells with increased differentiation. FIG. 2A (cytotoxicity and cytokines of $CD8^+$ T cell subsets, human blood gene expression) shows cytotoxic potential of T cells increases from TN→TCM→TEM→TEMRA. FIG. 2B (% $KLRG1^+$ $CD6^+$ T cells of human blood $CD8^+$ subpopulation by flow cytometry) shows KLRG1 expression increases from TN→TCM→TEM→TEMRA. As $CD8^+$ cytotoxic T cells differentiate in response to antigen, from naïve T cells to central memory, effector memory, and effector memory RA cells, they express increased amounts of KLRG1. Thus, KLRG1 marks cells with high capacity for cytotoxic killing. This cytotoxicity may be undesired (in the case of autoimmune disease and transplant rejection) or desired (in the case of cancer or chronic infectious disease).

As KLRG1 function in humans is substantially different than KLRG1 function in mice, mouse data is of limited applicability to the treatment of human disease. However, there is a near complete absence of published KLRG1 translational data in human diseases. There are no published studies of KLRG1 expression by immunohistochemistry in any human diseased or healthy tissue sample. There are 4 published studies that contain minor data on KLRG1 expression by flow cytometry in human diseased tissue samples, other than peripheral blood mononuclear cells (PBMCs): tumor-infiltrating lymphocytes in hepatocellular carcinoma (Brunner et al., 2015) and renal cell carcinoma (Attig et al., 2009); tumor infiltrated lymph node in melanoma (Legat et al., 2013); and synovial T cells in rheumatoid arthritis and spondyloarthropathies (Melis et al., 2014). Approximately 5 published studies contain minor data on KLRG1 expression in diseased PBMCs.

KLRG1 is a co-inhibitory receptor like a number of other T cell co-inhibitory receptors and, as such, can be compared to CTLA-4, PD-1, LAG-3, and TIM-3. Whereas these later co-inhibitory receptors have been recognized as markers of T cell exhaustion (Blackburn et al., 2009) and 2 of them (CTLA-4 and PD-1) successfully targeted via immunotherapies for the treatment of cancer (Mahoney et al., 2015), KLRG1 has not been recognized as an exhaustion marker, but rather as a marker of immunosenescence (Akbar and Henson, 2011, Apetoh et al., 2015). As a marker of immunosenescence, KLRG1 has been viewed as an unfavorable target for immunotherapy (Akbar and Henson, 2011).

Much of the science and attention to CTLA-4 and PD-1 as favorable targets for immunotherapy has developed as a consequence of studies of mouse biology. The demonstration that CTLA-4 knockout mice had lethal spontaneous systemic autoimmunity propelled attention to targeting this pathway to generate cancer autoimmunity (Tivol et al., 1995). The demonstration that PD-1 knockout mice had spontaneous autoimmunity similarly focused activity on PD-1 targeting for human therapeutic potential (Nishimura et al., 1999).

In contrast, KLRG1 expression in mice has been identified as negatively correlated with that of PD-1 (Blackburn et al., 2009). Unlike CTLA-4 and PD-1 knockout mice, KLRG1 knockout mice do not demonstrate spontaneous autoimmunity (Grundemann et al., 2010). Whereas multiple pharmaceutical industry-led clinical development programs exist for most other co-inhibitory T cell receptors (FIG. 3, drug development programs for co-inhibitory receptor modulation by pharmaceutical companies. Gray boxes indicate public domain program exists), no drug development program for KLRG1 is currently known in the public domain.

Furthermore, despite their characterization as senescent and being viewed as unfavorable for targeting for cancer immunotherapy, KLRG1$^+$ T cells can proliferate after modulation of the KLRG1 receptor with its ligands (Henson et al., 2009, Henson et al., 2012, Shi et al., 2014). Despite absence of a spontaneous autoimmune phenotype of KLRG1 knockout mice, these mice do show increased survival after *Mycobacterium tuberculosis* infection, suggesting heightened immunity in the absence of KLRG1 (Cyktor et al., 2013).

Figures 4A, 4B:
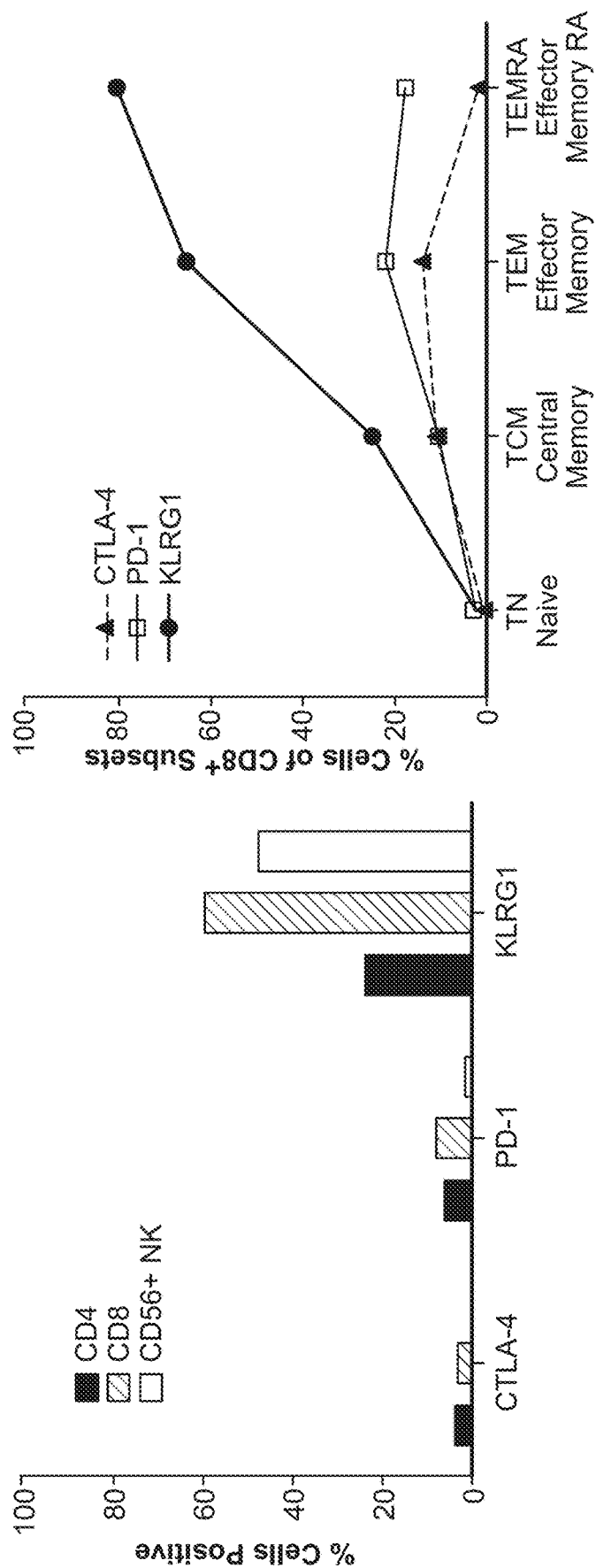
FIGS. 4A and 4B show CTLA-4 and PD-1 are more highly or similarly expressed on T helper cells (CD4$^+$) than cytotoxic T cells (CD8$^+$) or NK cells, while KRLG1 expression is higher on CD8$^+$ T and NK cells than CD4$^+$ T helper cells.

A goal of immune-oncology therapies is the activation of inhibited CD8$^+$ cytotoxic T and NK cells. Current FDA-approved drugs target CTLA-4 and PD-1. These molecules are more highly or similarly expressed on T helper cells (CD4$^+$) than cytotoxic T cells (CD8$^+$) or NK cells, while KRLG1 expression is higher on CD8$^+$ T and NK cells than CD4$^+$ T helper cells (FIGS. 4A and B). FIG. 4A (checkpoint expression of lymphocyte subset, human blood flow cytometry) shows proportionally greater expression of KLRG1 on lymphocyte subsets than CTLA-4 and PD-1. FIG. 4B (% cells of human blood CD8$^+$ subpopulation by flow cytometry) shows KLRG1 is expressed on a larger proportion of lymphocytes than CTLA-4 or PD-1 and increases from TN→TCM→TEM→TEMRA, while PD-1 and CTLA-4 expression decreases from TEM→TEMRA. Accordingly, one advantage of the present invention is the preferential targeting of CD8$^+$ cytotoxic T and/or NK cells. Another advantage is the targeting of the most potent (i.e., with greatest cytotoxic potential) subpopulations of CD8$^+$ cytotoxic T cells and of NK cells.

Figure 5:
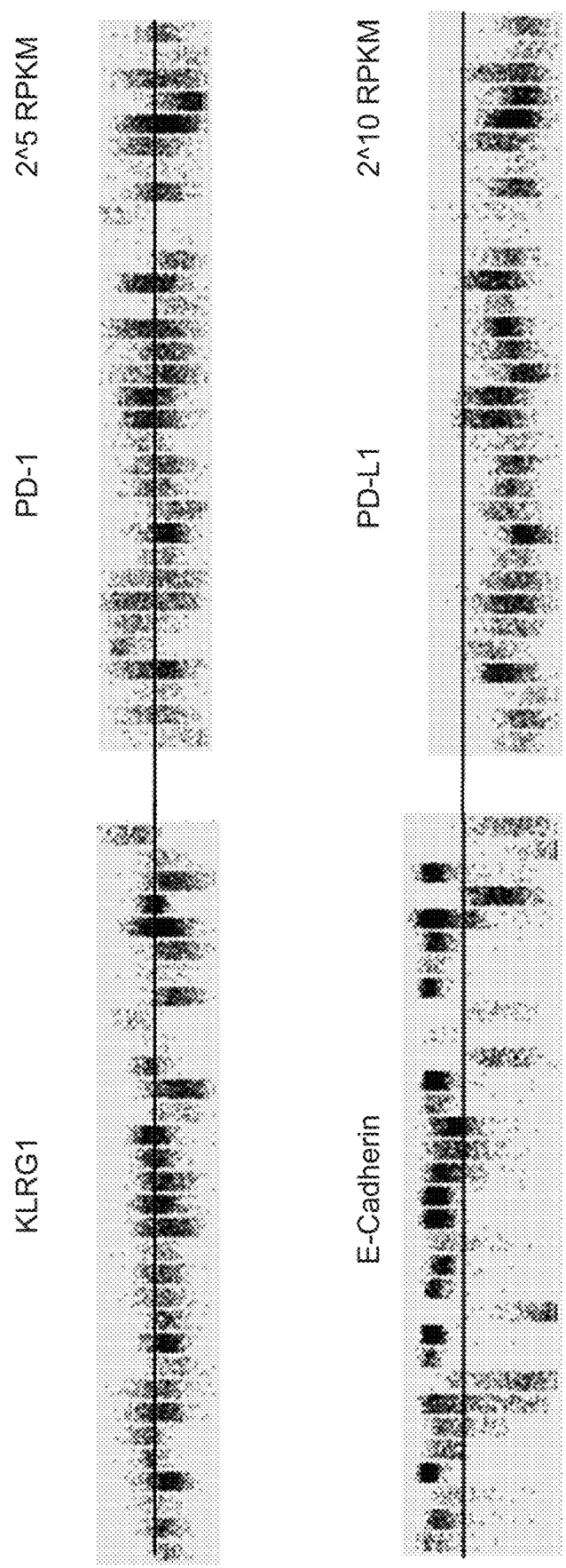
FIG. 5 shows the widespread infiltration of many tumor types by KLRG1 expressing T cells and expression of the KLRG1 ligand E-cadherin in these tumor samples.

With these new insights, further analysis of previously unanalyzed data demonstrates the widespread infiltration of many tumor types by KLRG1 expressing T cells and expression of the KLRG1 ligand E-cadherin in these tumor samples (FIG. 5, see also Examples 3 and 4 below). E-cadherin expression is substantially greater than that of the PD-1 ligand PD-L1 in a wide array of tumors.

In various aspects and embodiments, KLRG1 is human or cynomolgus KLRG1, preferably human KLRG1, including any functional part thereof. For example, KLRG1 can be Human-KLRG1-ECD-Isotype 1 (SEQ ID NO:1), including any functional part thereof.

In various aspects and embodiments, KLRG1 is Human-KLRG1-ECD-Isotype2 (SEQ ID NO:2), including any functional part thereof.

In various aspects and embodiments, KLRG1 is Cynomolgus-KLRG1 (SEQ ID NO:3), including any functional part thereof.

In various aspects and embodiments, KLRG1 ligand is a cadherin, preferably a human cadherin, including any functional parts thereof.

In various aspects and embodiments, KLRG1 ligand is human E-cadherin (SEQ ID NO:4), including any functional part thereof.

In various aspects and embodiments, KLRG1 ligand is human N-cadherin (SEQ ID NO:5), including any functional part thereof.

In various aspects and embodiments, KLRG1 ligand is human R-cadherin (SEQ ID NO:6), including any functional part thereof.

In some embodiments, the binding agent targets amino acids in KLRG1 sequence involved in binding cadherin. For example, in one embodiment, the binding agent binds (157) NSFVQ(162) and/or (172)QASSCEV(178) of SEQ ID NO:1 and SEQ ID NO:2, respectively.

Antagonists, Binding Agents

In various aspects and embodiments, a killer cell lectin-like receptor G1 (KLRG1) antagonist comprises (i) a killer cell lectin-like receptor G1 (KLRG1)/ligand binding agent or (ii) an RNAi agent that suppresses KLRG1 expression. In various aspects and embodiments, the binding agent is an antibody or antigen binding fragment thereof, or antibody mimetic. In general, the antagonist disrupts KLRG1 signaling, thereby achieving a therapeutic effect (e.g., by activating CD8$^+$ cytotoxic T and/or NK cells). In various embodiments, the antagonist binds the extracellular domain of human KLRG1 or binds a KLRG1 ligand (e.g., thus disrupting KLRG1 signaling).

The term "antibody" is used in the broadest sense and specifically covers, for example, single anti-KLRG1 or anti-KLRG1 ligand monoclonal antibodies. The term "monoclonal antibody" as used herein refers to an antibody obtained from a population of substantially homogeneous antibodies, e.g., the individual antibodies comprising the population are identical except for possible naturally-occurring mutations that may be present in minor amounts. An antibody can be monoclonal. An antibody can be a human or humanized antibody.

"Antibody fragments" can include a portion of an intact antibody, preferably the antigen binding or variable region of the intact antibody. Examples of antibody fragments include Fab, Fab', F(ab')2, and Fv fragments, diabodies, linear antibodies, single-chain antibody molecules, and multispecific antibodies formed from antibody fragments.

"Fv" includes the minimum antibody fragment which contains a complete antigen-recognition and binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. "Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domains which enables the sFv to form the desired structure for antigen binding.

In various embodiments, the antibody or antigen binding fragment thereof, or antibody mimetic comprises a human or humanized antibody. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin and all or substantially all of the FR regions are those of a human immunoglobulin consensus sequence. Methods for humanizing non-human antibodies are well known in the art.

The binding agents may also be affinity matured, for example using selection and/or mutagenesis methods known in the art. In general, an "affinity matured" antibody is one with one or more alterations in one or more hyper variable regions thereof which result in an improvement in the affinity of the antibody for antigen, compared to a parent antibody which does not possess those alteration(s). In one embodiment, an affinity matured antibody has nanomolar or even picomolar affinities for the target antigen. Preferred affinity matured antibodies have an affinity which is five times, more preferably 10 times, even more preferably 20 or 30 times greater than the starting antibody (generally murine, humanized or human) from which the matured antibody is prepared.

An antibody that "binds to," "specifically binds to," or is "specific for" a particular polypeptide or an epitope on a particular polypeptide is one that binds to that particular polypeptide or epitope on a particular polypeptide without substantially binding to any other polypeptide or polypeptide epitope. As such, a KLRG1/ligand binding agent includes functional equivalents to an anti-KLRG1/ligand antibody according to the invention. A KLRG1/ligand binding agent can be a binding agent that binds to or specifically binds to KLRG1 (e.g., human KLRG1). In some cases, the KLRG1/ligand binding agent may be cross reactive with various similar KLRG1 proteins (e.g., with highest affinity for one, such as human HLRG1, and lower affinity for others, such as mouse KLRG1). A KLRG1/ligand binding agent can be a binding agent that binds to or specifically binds to a KLRG1 ligand. Again, the KLRG1/ligand binding agent can be a binding agent that binds to or specifically binds to one, or in some cases cross reacts with more than one, KLRG1 ligand (e.g., one or more human cadherins).

In various embodiments, the binding agent is a blocking or antagonist binding agent. "Blocking" or "antagonist" means the agent (e.g., antibody or binding fragment/mimic thereof) is one which inhibits or reduces biological activity of the antigen it binds. Certain blocking agents or antagonist agents substantially or completely inhibit the biological activity of the antigen. For example, a KLRG1/ligand binding agent can block KLRG1 signaling (e.g., thereby disrupting KLRG1 signaling and activating $CD8^+$ cytotoxic T and/or NK cells). Example 21 presents one example methodology for identifying and/or characterizing antibodies with neutralizing activity.

In various embodiments, the antibody or antigen binding fragment thereof, or antibody mimetic comprises:

a. a full length antibody Fab portion that binds KLRG1;

b. a full length antibody Fab portion that binds E-cadherin;

c. a full length antibody Fab portion that binds N-cadherin;

d. a full length antibody Fab portion that binds R-cadherin;

e. a fusion protein E-cadherin/Fc;

f. a fusion protein R-cadherin/Fc;

g. a fusion protein N-cadherin/Fc;

h. a chimeric antigen receptor; or i. a multispecific antibody.

In various embodiments, the binding agent is a chimeric antigen receptor and the chimeric antigen receptor comprises a specificity portion of a KLRG1 antibody grafted onto a T cell.

In various embodiments, the binding agent is a multispecific antibody. The multispecific antibody can comprise a bispecific or trispecific antibody.

In various embodiments, the binding agent binds KLRG1.

In various embodiments, the KLRG1 is the extracellular domain of human KLRG1.

In various embodiments, the binding agent binds a KLRG1 ligand.

In various embodiments, the KLRG1 ligand is human E-cadherin, N-cadherin, or R-cadherin.

In various embodiments, the binding agent binds KLRG1 and/or cadherin at a KLRG1/cadherin binding site.

In various embodiments, the binding agent is not a prior art antibody. Known anti-KLRG1 antibodies include clone 13F12F2 (eBioscience), which is a mouse anti-human KLRG1 antibody that binds to the extracellular domain and has demonstrated reactivity against human cells in flow cytometry, clones 14C2A07 (Biolegend) and SA231A2 (Biolegend), which are reported to be anti-human KLRG1 antibodies, and clone 2F1, which is a hamster anti-mouse KLRG1 antibody that some vendors (e.g., Biolegend) report to be reactive against human while others (e.g., Abcam) report reactivity to only mouse. Tests of these antibodies failed to demonstrate reactivity to human KLRG1. Clone 13A2 (EBioscience) is said to bind a similar epitope to clone 13F12F2. Clone REA261 (Miltenyi Biotec) also reportedly binds human KLRG1. (Binding not verified.) Known anti-E-cadherin antibodies are described by vendors and include the following examples: clone 67A4, clone MB2, and clone HECD1 (all sold by Abcam); DECMA1 sold by eBioscience; and clone 36/E-cadherin sold by BD Biosciences. In various embodiments, the KLRG1 antagonist comprises a binding agent that binds to KLRG1 and that is not clone 13F12F2, 14C2A07, SA231A2, 2F1, 13A2, or REA261 (or another previously described anti-KLRG1 antibody).

In various embodiments, the KLRG1/ligand binding agent can be administered by providing an mRNA encoding the binding agent to the subject. Such mRNA approaches are being developed by Moderna Therapeutics and the like.

In various embodiments, the KLRG1 antagonist comprises a binding agent that blocks or competes with KLRG1-ligand binding.

In various embodiments, the KLRG1 antagonist comprises a binding agent that cross reacts with the extracellular domains of human and cynomolgus KLRG1, or the human and cynomolgus KLRG1 ligand.

In various embodiments, the KLRG1 antagonist comprises a binding agent that binds to an epitope of (i) the extracellular domain of KLRG1 or (ii) the KLRG1 ligand, wherein the epitope is at least 90% identical in human and cynomolgus. In one embodiment, the KLRG1 antagonist comprises a binding agent that binds to the same epitope as any one of clone 13F12F2, 14C2A07, SA231A2, 2F1, 13A2, or REA261.

In various embodiments, the KLRG1 antagonist comprises a binding agent that binds to KLRG1 and that is not a mouse antibody.

In various embodiments, the antagonist neutralizes KLRG1/E-cadherin binding.

In various embodiments, the invention provides a killer cell lectin-like receptor G1 (KLRG1)/ligand binding agent that neutralizes KLRG1/cadherin (e.g., E-cadherin) binding and disrupts KLRG1 signaling, thereby activating CD8$^+$ cytotoxic T and/or NK cells.

In various embodiments, the antagonist or binding agent cross competes with at least one of clone 13F12F2, 14C2A07, SA231A2, 2F1, 13A2, or REA261.

In various embodiments, the binding agent is a human or humanized monoclonal antibody, or binding fragment thereof.

In various embodiments, the KLRG1 antagonist comprises an RNAi agent. The RNAi agent can be, inter alia, an siRNA or an mRNA.

Like antibodies (and their equivalents), RNAi agents that can be applied in the present invention are known in the art. Briefly, RNA interference (RNAi) is a biological process in which RNA molecules inhibit gene expression, typically by causing the destruction of specific mRNA molecules. RNAi is now known as precise, efficient, stable and better than antisense technology for gene suppression. Two types of small ribonucleic acid (RNA) molecules—microRNA (miRNA) and small interfering RNA (siRNA)—are central to RNA interference. RNAs are the direct products of genes, and these small RNAs can bind to other specific messenger RNA (mRNA) molecules and either increase or decrease their activity, for example by preventing an mRNA from producing a protein. However, the present invention is not necessarily limited to siRNA and mRNA.

Checkpoint Modulator Therapy

In various embodiments, the methods further comprise administering to the subject an effective amount of a checkpoint modulator therapy. As used herein, the term "checkpoint modulator therapy" includes agents that have a therapeutic effect through modulation of immune system function (e.g., for treating cancer). Immune checkpoints can be stimulatory or inhibitory. Checkpoint therapy can block inhibitory checkpoints (e.g., when used by cancer to evade the immune system), restoring immune system function. Examples of approved and commercially available checkpoint modulator therapies include Pembrolizumab (Keytruda®), Nivolumab (Opdivo®), and Ipilimumab (Yervoy®). Numerous other checkpoint modulator therapies are under development and in clinical trials (see, e.g., FIG. 3).

The checkpoint modulator therapy and the KLRG1/ligand binding agent can be administered to the subject essentially simultaneously (e.g., concurrently, during the same day, during the same course of treatment) or within a time period where the checkpoint modulator therapy and the KLRG1/ligand binding agent combine favorably to achieve a desired effect (e.g., effective treatment, synergy). Some checkpoint modulators may induce KLRG1 expression that counteracts the modulators' effectiveness; combining with KLRG1 would restore their effectiveness. In various embodiments, the KLRG1/ligand binding agent and checkpoint modulator therapy are synergistic. Synergy can be defined as the combination having greater than an additive (or otherwise expected) effect, which can be measured by various methods known in the art.

In various embodiments, the checkpoint modulator therapy is Pembrolizumab (Keytruda®; anti-PD-1). Without limitation, in such embodiments, the cancer can be lung cancer (e.g., non-small cell lung cancer) or melanoma (e.g., metastatic melanoma).

In various embodiments, the checkpoint modulator therapy is Nivolumab (Opdivo®). Without limitation, in such embodiments, the cancer can be lung cancer (e.g., non-small cell lung cancer) or melanoma (e.g., metastatic melanoma) or kidney cancer (e.g., renal cell carcinoma).

In various embodiments, the checkpoint modulator therapy is Ipilimumab (Yervoy®). Without limitation, in such embodiments, the cancer can be melanoma (e.g., metastatic melanoma or stage III melanoma).

In various embodiments, the checkpoint modulator therapy is PF-05082566 (Pfizer; anti-4-1BB agonist). Without limitation, in such embodiments, the cancer can be a solid tumor or a melanoma (e.g., metastatic melanoma).

In various embodiments, the checkpoint modulator therapy is Urelumab (BMS; anti-4-1BB agonist). Without limitation, in such embodiments, the cancer can be a solid tumor, head and neck cancer, or melanoma (e.g., metastatic melanoma).

In various embodiments, the checkpoint modulator therapy is Atezolizumab (Roche; anti-PD-L1). Without limitation, in such embodiments, the cancer can be a solid tumor, locally advanced or metastatic urothelial carcinoma or lung cancer (e.g., non-small cell lung cancer) or bladder cancer.

In various embodiments, the checkpoint modulator therapy is Durvalumab (MedImmune; anti-PD-L1). Without limitation, in such embodiments, the cancer can be a solid tumor, lung cancer (e.g., non-small cell lung cancer), or melanoma (e.g., metastatic melanoma).

In various embodiments, the checkpoint modulator therapy is Tremilimumab (Astra-Zeneca; anti-CTLA-4). Without limitation, in such embodiments, the cancer can be a solid tumor, non-small cell lung cancer (e.g., NSCLC), squamous cell carcinoma (e.g., of the head and neck), melanoma (e.g., metastatic melanoma), bladder cancer, pancreatic cancer, gastric cancer, or liver cancer (e.g., HCC).

In various embodiments, the checkpoint modulator therapy is BMS986016 (BMS; anti-LAG-3). Without limitation, in such embodiments, the cancer can be a solid tumor or melanoma (e.g., metastatic melanoma).

In various embodiments, the checkpoint modulator therapy is MGB453 (Novartis; anti-TIM-3). Without limitation, in such embodiments, the cancer can be a solid tumor or melanoma (e.g., metastatic melanoma).

Notwithstanding the foregoing illustrative examples, one skilled in the art will appreciate that the KLRG1/ligand binding agent can be combined with other checkpoint modulator therapies and/or used for different indications.

Cancer Vaccine Therapy

In various embodiments, the method further comprises administering to the subject an effective amount of a cancer vaccine therapy. As used herein, the term "cancer vaccine therapy" includes agents that stimulate an immune system response for treating cancer. The term "cancer vaccine therapy" does not include vaccines against pathogens that may later cause cancer (e.g., a hepatitis vaccine that prevents hepatitis, but not a subsequent liver cancer where a hepatitis infection was a causative factor). Examples of approved and commercially available cancer vaccine therapies include Sipuleucel-T (Provenge®) for prostate cancer. Other cancer vaccine therapies are under development and in clinical trials.

The cancer vaccine therapy and the KLRG1/ligand binding agent can be administered to the subject essentially simultaneously (e.g., concurrently, during the same day, during the same course of treatment) or within a time period where the cancer vaccine therapy and the KLRG1/ligand binding agent combine favorably to achieve a desired effect (e.g., effective treatment, synergy). In some embodiments, the anti-KLRG1 therapy allows for a more effective T cell response to the vaccine. In various embodiments, the KLRG1/ligand binding agent and cancer vaccine therapy are synergistic. Synergy can be defined as the combination having greater than an additive (or otherwise expected) effect, which can be measured by various methods known in the art.

In various embodiments, the cancer vaccine therapy is Sipuleucel-T (Provenge®). Without limitation, in such embodiments, the cancer can be prostate cancer.

In various embodiments, the cancer vaccine therapy is INO-3112 (Inovio). Without limitation, in such embodiments, the cancer can be a human papilloma virus (HPV) driven cancer (e.g., head and neck cancer).

In various embodiments, the cancer vaccine therapy is INO-5150 (Inovio). Without limitation, in such embodiments, the cancer can be prostate cancer.

In various embodiments, the cancer vaccine therapy is TPIV 200 (TapImmune). Without limitation, in such embodiments, the cancer can be ovarian cancer.

Notwithstanding the foregoing illustrative examples, one skilled in the art will appreciate that the KLRG1/ligand binding agent can be combined with other cancer vaccine therapies and/or used for different indications.

Other Active Pharmaceutical Ingredients

In various embodiments, the invention can use a combination of the KLRG1/ligand binding agent and one or more additional Active Pharmaceutical Ingredient (API). Accordingly, the invention can increase the efficacy of, and/or decrease undesired side effects from, the KLRG1/ligand binding agent.

In various embodiments, the method further comprises administering to the subject an effective amount of a cancer chemotherapy.

In various embodiments, the checkpoint modulator therapy comprises an anti-PD-1, anti-PD-L1, or anti-CTLA-4 therapy.

In various embodiments, the subject has failed or has not responded to a prior cancer therapy.

In various embodiments, the subject has elevated KLRG1 expression. The elevated KLRG1 expression can comprise elevated KLRG1 expression on $CD8^+$ cytotoxic T and/or NK cells. In various embodiments, the method can further comprise testing the subject for elevated KLRG1 expression (e.g., before beginning and/or during the therapy).

In various embodiments, the subject has elevated cadherin expression (e.g., E-cadherin). The elevated cadherin expression can comprise elevated cadherin expression on cancer cells. In various embodiments, the method can further comprise testing the subject for elevated cadherin expression (e.g., before beginning and/or during the therapy).

In some embodiments, the API may be a polynucleotide (including an oligonucleotide) a protein or a small molecule.

In one embodiment the API is a polynucleotide. The polynucleotide may be a genomic DNA fragment, cDNA, mRNA, ssRNA, dsRNA, microRNA, siRNA, shRNA, sdRNA, DsiRNA, LNA, and antisense DNA or RNA.

Alternatively, the API may be a small molecule drug. Preferably, the molecule has a molecular weight from about 1500 g/mol to about 50 g/mol.

An API can include, for example, two or more of the following: an anticancer agent, an antibiotic agent, an antiviral agent, an anti-fungal agent, or an analgesic.

Exemplary anticancer agents may include but are not limited acivicin, aclarubicin, acodazole, ametantrone, aminoglutethimide, anthramycin, asparaginase, azacitidine, azetepa, bisantrene, bleomycin, busulfan, cactinomycin, calusterone, caracemide, carboplatin, carfilzomib, carmustine, carubicin, chlorambucil, cisplatin, cyclophosphamide, cytarabine, dacarbazine, dactinomycin, daunorubicin, dezaguanine, diaziquone, docetaxel, doxorubicin, epipropidine, erlotinib, etoposide, etoprine, floxuridine, fludarabine, fluorouracil, fluorocitabine, hydroxyurea, iproplatin, leuprolide acetate, lomustine, mechlorethamine, megestrol acetate, melengestrol acetate, mercaptopurine, methotrexate, metoprine, mitocromin, mitogillin, mitomycin, mitosper, mitoxantrone, mycophenolic acid, nocodazole, nogalamycin, oxisuran, paclitaxel, peliomycin, pentamustine, porfiromycin, prednimustine, procarbazine hydrochloride, puromycin, pyrazofurin, riboprine, semustine, sparsomycin, spirogermanium, spiromustine, spiroplatin, streptozocin, talisomycin, tegafur, teniposide, teroxirone, thiamiprine, thioguanine, tiazofurin, triciribine phosphate, triethylenemelamine, trimetrexate, uracil mustard, uredepa, vinblastine, vincristine, vindesine, vinepidine, vinrosidine, vinzolidine, zinostatin and zorubicin.

Exemplary antibiotic agents may include but are not limited to aminoglycoside; amikacin; gentamicin; kanamycin; neomycin; netilmicin; steptomycin; tobramycin; ansamycins; geldanamycin; herbimycin; carbacephem; loracarbef; carbacepenem; ertapenem; doripenem; imipenem/cilastatin; meropenem; cephalosporin; cefadroxil; cefazolin; cefalotin or cefalothin; cefalexin; cefaclor; cefamandole; cefoxitin; cefprozil; cefuroxime; cefixime; cefdinir; cefditoren; cefoperazone; cefotaxime; cefpodoxime; ceftazidime; ceftibuten; ceftizoxime; ceftriaxone; cefepime; ceftobiprole; glycopeptide; teicoplanin; vancomycin; macrolides; azithromycin; clarithromycin; dirithromycin; erythromycin; roxithromycin; troleandomycin; telithromycin; spectinomycin; monobactam; aztreonam; penicillins; amoxicillin; ampicillin; azlocillin; carbenicillin; cloxacillin; dicloxacillin; flucloxacillin; mezlocillin; meticillin; nafcillin; oxacillin; penicillin, piperacillin, ticarcillin; bacitracin; colistin; polymyxin B; quinolone; ciprofloxacin; enoxacin; gatifloxacin; levofloxacin; lomefloxacin; moxifloxacin; norfloxacin; ofloxacin; trovafloxacin; sulfonamide; mafenide; prontosil (archaic); sulfacetamide; sulfamethizole; sufanilimide (archaic); sulfasalazine; sulfisoxazole; trimethoprim; trimethoprim-sulfamethoxazole (co-trimoxazole) (TMP-SMX); tetracycline; demeclocycline; doxycycline; minocycline; oxytetracycline; tetracycline; arsphenamine; chloramphenicol; clindamycin; lincomycin; ethambutol; fosfomycin; fusidic acid; furazolidone; isoniazid; linezolid; metronidazole; mupirocin; nitrofuantoin; platensimycin; polymyxin, purazinamide; quinupristin/dalfopristin; rifampin or rifampicin; and timidazole.

In specific embodiments, the anti-cancer agent is chosen from daunorubicin, doxorubicin, paclitaxel, docetaxel, cisplatin, carboplatin, cytarabine, floxuridine, fludarabine, fluorouracil, iproplatin, leuprolide acetate, carfilzomib, and methotrexate.

Exemplary antiviral agents may include, but are not limited to thiosemicarbazone; metisazone; nucleoside and/or nucleotide; acyclovir; idoxuridine; vidarabine; ribavirin; ganciclovir; famciclovir; valaciclovir; cidofovir; penciclovir; valganciclovir; brivudine; ribavirin, cyclic amines; rimantadine; tromantadine; phosphonic acid derivative; foscamet; fosfonet; protease inhibitor; saquinavir; indinavir; ritonavir; nelfinavir; amprenavir; lopinavir; fosamprenavir; atazanavir; tipranavir; nucleoside and nucleotide reverse transcriptase inhibitor; zidovudine; didanosine; zalcitabine; stavudine; lamivudine; abacavir; tenofovir disoproxil; adefovir dipivoxil; emtricitabine; entecavir; non-nucleoside reverse transcriptase inhibitor; nevirapine; delavirdine; efavirenz; neuraminidase inhibitor; zanamivir; oseltamivir; moroxydine; inosine pranobex; pleconaril; and enfuvirtide.

Exemplary anti-fungal agents may include but are not limited to allylamine; terbinafine; antimetabolite; flucytosine; azole; fluconazole; itraconazole; ketoconazole; ravuconazole; posaconazole; voriconazole; glucan synthesis inhibitor; caspofungin; micafungin; anidulafungin; polyenes; amphotericin B; amphotericin B Colloidal Dispersion (ABCD); and griseofulvin.

Exemplary analgesics may include, but are not limited to opiate derivative, codeine, meperidine, methadone, and morphine.

Pharmaceutical Compositions

In various embodiments, the KLRG1/ligand binding agent is prepared as a pharmaceutical composition, for example as a pharmaceutical composition for use as a medicament. In various embodiments, the pharmaceutical composition is for use as a cancer therapeutic. In various embodiments, the pharmaceutical composition can include one or more antibiotic, antivirus, anti-diabetes, anti-hypertension, anti-fungal, or analgesic.

One skilled in the art can formulate the KLRG1/ligand binding agent as a pharmaceutical composition according to known methods.

Pharmaceutical compositions can include a carrier. "Carriers" as used herein can include pharmaceutically acceptable carriers, excipients, or stabilizers which are nontoxic (or relatively non-toxic) to the cell or subject being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

In various embodiments, the KLRG1/ligand binding agent is comprised in an injectable formulation, for example, a subcutaneous, intravenous, intramuscular, intrathecal or intraperitoneal injection formulation. Injectable formulations can be aqueous solutions, for example in physiologically compatible buffers such as Hanks' solution, Ringer's solution, or physiological saline buffer. The injectable formulation can contain formulatory agents such as suspending, stabilizing and/or dispersing agents. Alternatively, the KLRG1/ligand binding agent can be in a dried or powder form for constitution with a suitable vehicle, e.g., sterile pyrogen-free water, before use.

Treatment and Administration, Cancers

The invention provides methods comprising administering the KLRG1/ligand binding agent according to any of the aspects or embodiments disclosed herein, or the pharmaceutical composition according to any of the aspects or embodiments disclosed herein, to a subject in need thereof. In various embodiments, the subject is a human. In various embodiments, methods according to the invention are carried out in vivo (e.g., as opposed to ex vivo). As used herein, "treatment" can refer to both therapeutic treatment and prophylactic or preventative measures, wherein the object is to prevent or slow down (lessen) the targeted pathologic condition or disorder. Those in need of treatment can include those already with the disorder, those prone to have the disorder, or those in whom the disorder is to be prevented.

In various aspects and embodiments, the invention provides a method of treating a subject comprising administering to a subject in need thereof an effective amount of a killer cell lectin-like receptor G1 (KLRG1)/ligand binding agent, thereby disrupting KLRG1 signaling and activating CD8$^+$ cytotoxic T and/or NK cells.

The invention provides a method of treating cancer comprising administering to a subject in need thereof an effective amount of a killer cell lectin-like receptor G1 (KLRG1)/ligand binding agent.

"Administration" and "treatment," as it applies to an animal, human, experimental subject, cell, tissue, organ, or biological fluid, can include contacting an exogenous pharmaceutical, therapeutic agent, diagnostic agent, or composition to the animal, human, subject, cell, tissue, organ, or biological fluid. "Administration" and "treatment" include in vivo, as well as in some embodiments in vitro or ex vivo treatments.

"Treat" or "treating" means to administer a therapeutic agent, such as a composition containing any of the binding agents of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom.

As such, in various embodiments, the term "effective amount" is a concentration or amount of the KLRG1/ligand binding agent which results in achieving a particular stated purpose. An "effective amount" of a KLRG1/ligand binding agent can be determined empirically. Furthermore, a "therapeutically effective amount" is a concentration or amount of a KLRG1/ligand binding agent which is effective for achieving a stated therapeutic effect. This amount can also be determined empirically.

The invention provides a method of treating a melanoma comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating $CD8^+$ cytotoxic T and/or NK cells.

The invention provides a method of treating a lung cancer comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating $CD8^+$ cytotoxic T and/or NK cells.

The invention provides a method of treating a pancreatic cancer comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating $CD8^+$ cytotoxic T and/or NK cells.

The invention provides a method of treating a glioma comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating $CD8^+$ cytotoxic T and/or NK cells.

The invention provides a method of treating a breast cancer comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating $CD8^+$ cytotoxic T and/or NK cells.

The invention provides a method of treating an ovarian cancer comprising administering to a subject in need thereof an effective amount of a killer cell lectin-like receptor G1 (KLRG1)/ligand binding agent, wherein the binding agent is an antibody or antigen binding fragment thereof, or antibody mimetic that binds the extracellular domain of human KLRG1 and/or human E-cadherin, N-cadherin, or R-cadherin, thereby disrupting KLRG1 signaling and activating $CD8^+$ cytotoxic T and/or NK cells.

More generally, the invention provides methods for treating cancer cells and/or tissue, including cancer cells and/or tissue in a subject. Cancer can be caused by malignant tumors formed by an abnormal growth of cells and tissue leading to organ failure.

In various embodiments, the subject has an epithelial cancer.

In various embodiments, the subject has a carcinoma.

Solid tumors can be neoplasms (new growth of cells) or lesions (damage of anatomic structures or disturbance of physiological functions) formed by an abnormal growth of body tissue cells other than blood, bone marrow or lymphatic cells. A solid tumor consists of an abnormal mass of cells which may stem from different tissue types such as melanoma, lung, pancreatic, glioma, breast, or ovarian, and which initially grows in the organ of its cellular origin. However, such cancers may spread to other organs through metastatic tumor growth in advanced stages of the disease.

The subject being treated may have been diagnosed with cancer. The subject may have locally advanced, unresectable, or metastatic cancer and/or may have failed a prior first-line therapy.

In various embodiments, the subject has a uveal melanoma, uterine carcinoma, uterine carcinosarcoma, thyroid carcinoma, thymoma, testicular germ cell tumor, melanoma, sarcoma, rectal adenocarcinoma, prostate cancer, pheochromocytoma, pancreatic adenocarcinoma, ovarian cystadenocarcinoma, mesothelioma, lung squamous cell carcinoma, lung adenocarcinoma, liver hepatocellular carcinoma, kidney papillary cell carcinoma, kidney clear cell carcinoma, kidney chromophobe carcinoma, head and neck squamous cell carcinoma, glioblastoma multiforme, diffuse large B-cell lymphoma, colon adenocarcinoma, cholangiocarcinoma, cervical and/or endocervical cancer, breast invasive carcinoma, brain low grade glioma, bladder cancer, or acute myeloid leukemia.

In various embodiments, the subject has a melanoma.

In various embodiments, the subject has a lung cancer.

In various embodiments, the subject has a pancreatic cancer.

In various embodiments, the subject has a glioma.

In various embodiments, the subject has a breast cancer.

In various embodiments, the subject has an ovarian cancer.

In various embodiments, the KLRG1/ligand binding agent can be administered by providing an mRNA encoding the binding agent to the subject.

In various embodiments, the treatment can prolong the subject's survival. In various embodiments, the treatment can prevent or reduce the progression or the cancer and/or metastasis.

The following examples are illustrative and not restrictive. Many variations of the technology will become apparent to those of skill in the art upon review of this disclosure. The scope of the technology should, therefore, be determined not with reference to the examples, but instead should be determined with reference to the appended claims along with their full scope of equivalents.

EXAMPLES

Example 1: Antibodies to KLRG1

Antibodies binding KLRG1 were generated by immunization of mice with purified recombinant protein antigens: Human-KLRG1-ECD-Isotype 1 (SEQ ID NO:1), Human-KLRG1-ECD-Isotype2 (SEQ ID NO:2), and Cynomolgus-KLRG1 (SEQ ID NO:3). Mice were immunized every 2 weeks and sera collected for testing after the second and fourth immunization.

Figure 6A:
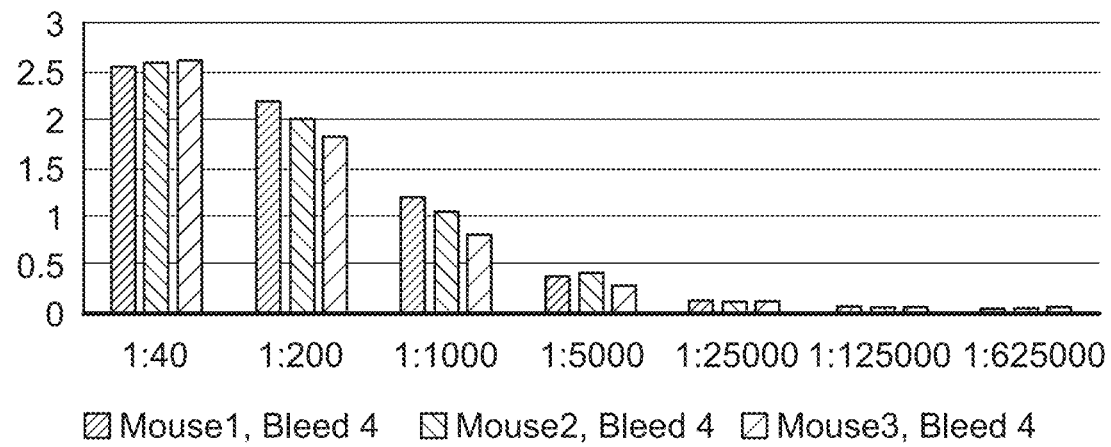
FIGS. 6A and 6B show sera responses of immunized mice to KLRG1.
Figure 6B:
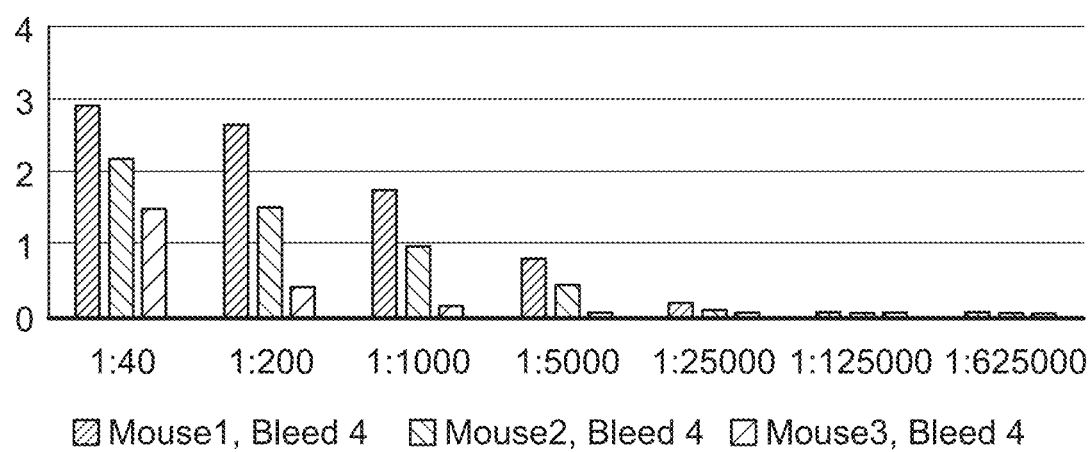

FIG. 6A show a specific serum response to the cynomolgus KLRG1 in the immunized mice. FIG. 6B show a specific serum response to the human KLRG1 in the immunized mice. Anti-KLRG1 antibody activity was measured by ELISA. The response was shown to be mediated by production of antibodies in the mouse recognizing human and cynomolgus KLRG1.

Figure 7:
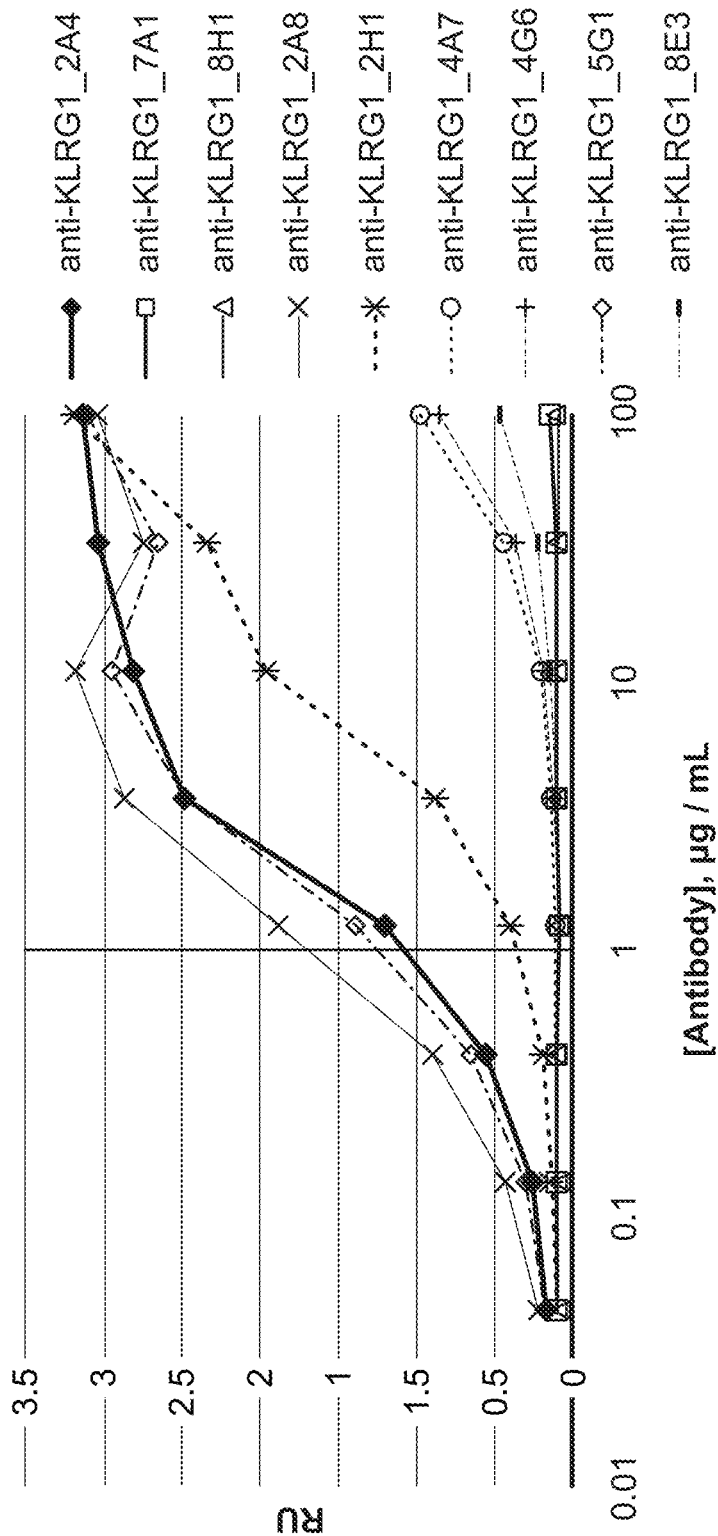
FIG. 7 shows binding of antibodies derived from hybridoma clones to human KLRG1 extracellular domain.

FIG. 7 shows a dose-dependent binding curve of 9 hybridoma clones isolated from immunized mice. ELISA was performed by first immobilizing human KLRG1 (SEQ ID NO 2) on immunosorbent 96-well plates, followed by exposure to a dose-dependent titration of antibodies. Bound antibodies were visualized by anti-mouse-HRP conjugated detection. Thus, FIG. 7 shows that splenocytes isolated from the spleens of immunized mice are able to produce antibodies that recognize KLRG1.

Example 2: Gene Expression of KLRG1 is Higher Among CD8$^+$ and NK Cells than CD4$^+$ T Cells, Correlates with CD8$^+$ T Cell Cytotoxic Potential, and is Higher than that of Checkpoint Co-Inhibitory Receptors CTLA-4 and PD-1

Figure 8:
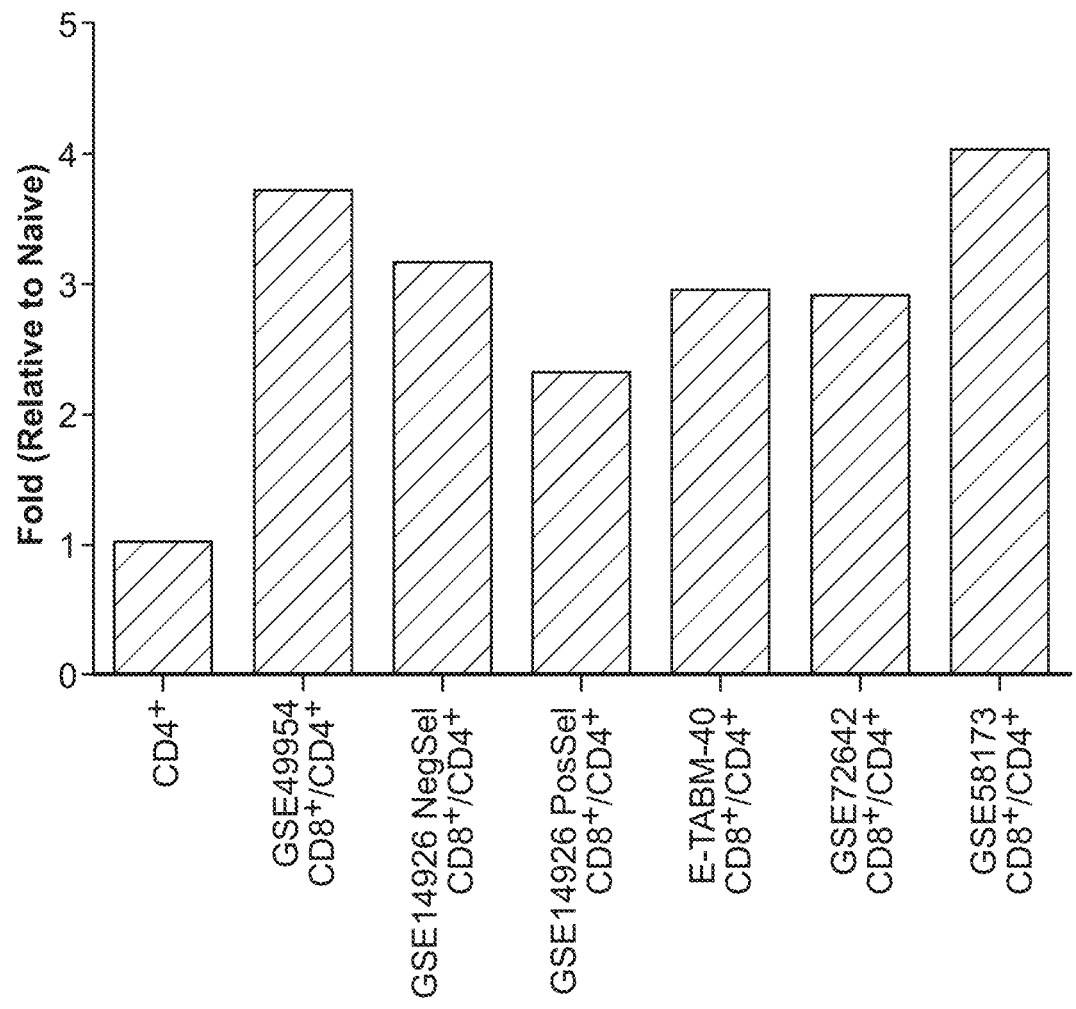
FIG. 8 shows an analysis of gene expression datasets that demonstrates higher expression of KLRG1 in CD8$^+$ cells compared to CD4$^+$ T helper cells.
Figure 9B:
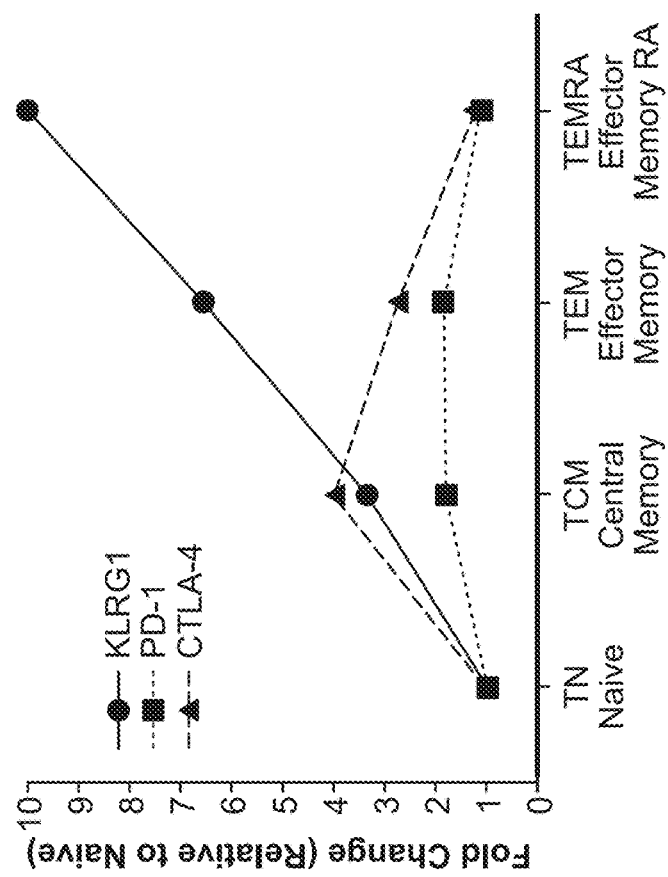
FIGS. 9A and 9B shows that the cytotoxic potential of CD8$^+$ T cells, as reflected by gene expression of cytotoxic molecules granzymes and cytokines, is highly correlated with expression of KLRG1 but not other checkpoint inhibitor target co-inhibitory receptors.
Figure 9A:
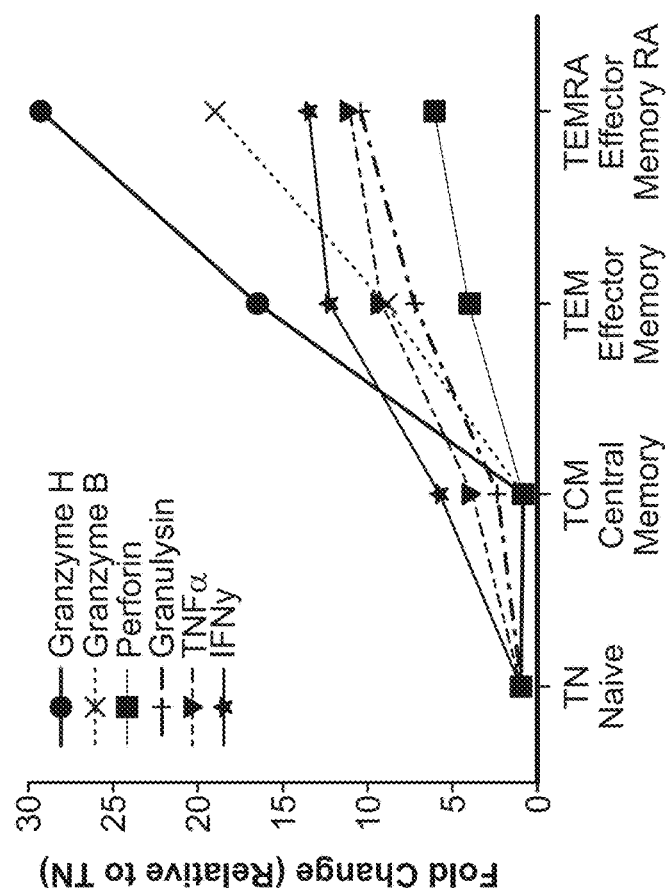

Analysis of gene expression datasets demonstrates the higher expression of KLRG1 in CD8$^+$ (relative-fold 4.0) cells compared to CD4$^+$ T helper cells (relative-fold 1.0) (FIG. 8, KLRG1 gene expression in human blood CD8$^+$ T cells). In response to antigen exposure, CD8$^+$ cytotoxic T cells differentiate from naïve cells to increasingly potent effector cells, characterized by central memory (TCM), effector memory (TEM), and effector (TEMRA) cells. The cytotoxic potential of CD8$^+$ T cells within these differentiation subsets, as reflected by gene expression of cytotoxic molecules granzymes and cytokines, is highly correlated with expression of KLRG1 but not other checkpoint inhibitor target co-inhibitory receptors PD-1 and CTLA-4 (see FIG. 9A, cytotoxicity and cytokines of CD8$^+$ T cell subsets, human blood gene expression and FIG. 9B, checkpoint expression of CD8$^+$ T cell subsets, human blood gene expression).

Example 3: Increased Expression of KLRG1 in Human Cancer

Microarray data from the Gene Expression Omnibus (GEO) and European Bioinformatics Institute (EBI) were compiled, normalized, and analyzed for fold-differences and significance levels. Datasets used were: E-TABM-40, GSE49954, GSE26495, GSE14926, GSE72642, GSE58173, GSE65010, GSE11507; TCGA data (at cancergenome.nih.gov/), and GTEX data (at www.gtexportal.org/).

KLRG1 is expressed by tumor infiltrating lymphocytes in a wide variety of cancer, as detected by RNAseq expression. FIG. 5 shows expression of KLRG1 and its ligand E-cadherin, compared with expression of PD-1 and its ligand PD-L1 in tumor samples in many cancer types (9,755 samples and 32 cancer types). Cancer types listed from left to right are: uveal melanoma, uterine carcinoma, uterine carcinosarcoma, thyroid carcinoma, thymoma, testicular germ cell tumor, melanoma, sarcoma, rectal adenocarcinoma, prostate cancer, pheochromocytoma, pancreatic adenocarcinoma, ovarian cysadenocarcinoma, mesothelioma, lung squamous cell carcinoma, lung adenocarcinoma, liver hepatocellular carcinoma, kidney papillary cell carcinoma, kidney clear cell carcinoma, kidney chromophobe, head and neck squamous cell carcinoma, glioblastoma multiforme, diffuse large B-cell lymphoma, colon adenocarcinoma, cholangiocarcinoma, cervical and endocervical cancer, breast invasive carcinoma, brain low grade glioma, bladder cancer, and acute myeloid leukemia. Without wishing to be bound by any particular theory, these cancers are particularly promising targets for use with the present invention because they are known to be immunogenic (e.g., melanoma, lung cancer, colon cancer, head and neck cancer). Their high expression of E-cadherin indicates their potential active invasion of immune attack by KLRG1$^+$ T and NK cells. Accordingly, such cancers are particularly attractive targets for therapies according to the present invention.

Example 4: Increased Expression of E-Cadherin in Human Cancer

Figure 10:
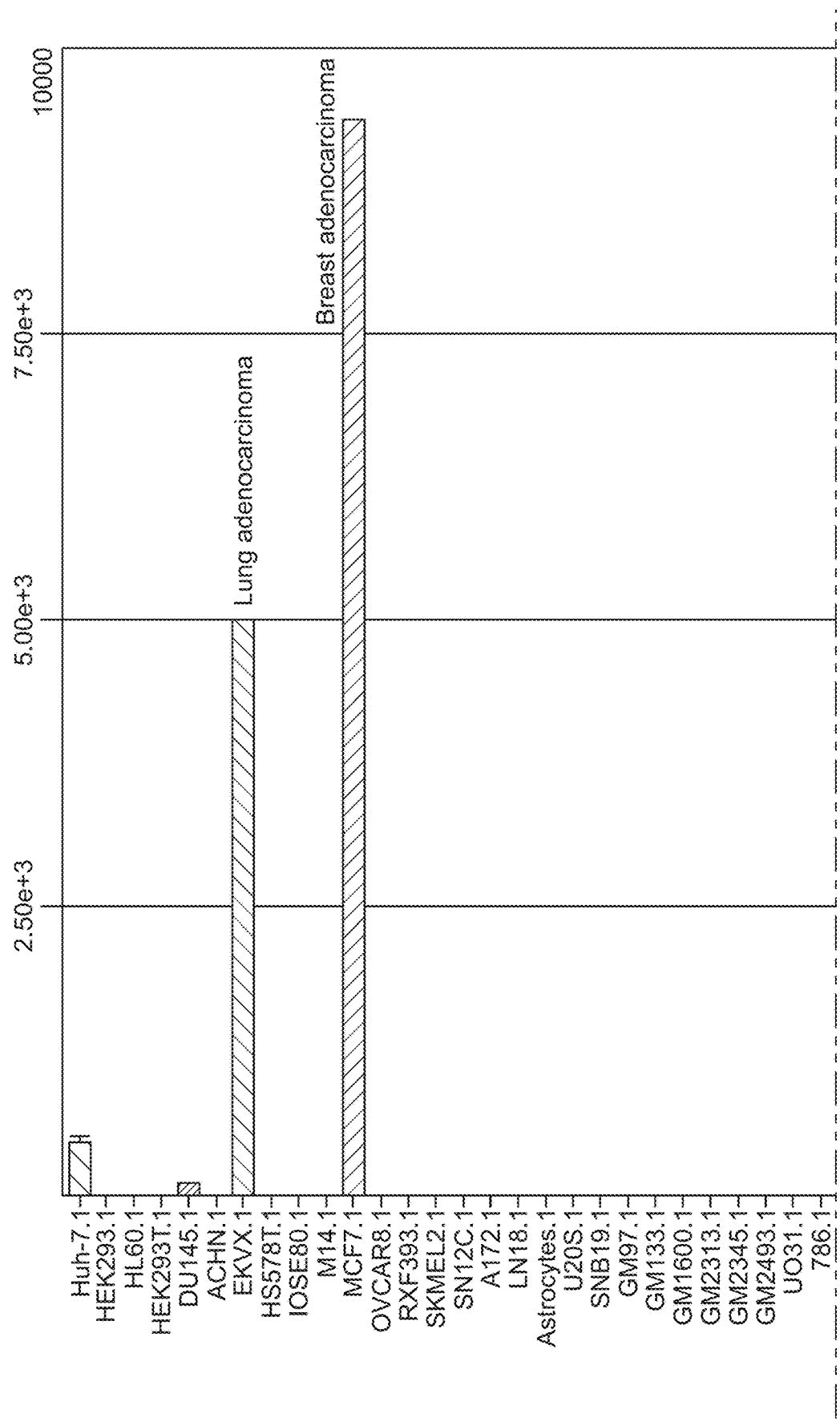
FIG. 10 shows E-cadherin is overexpressed in various cancer cell lines.
Figure 10:
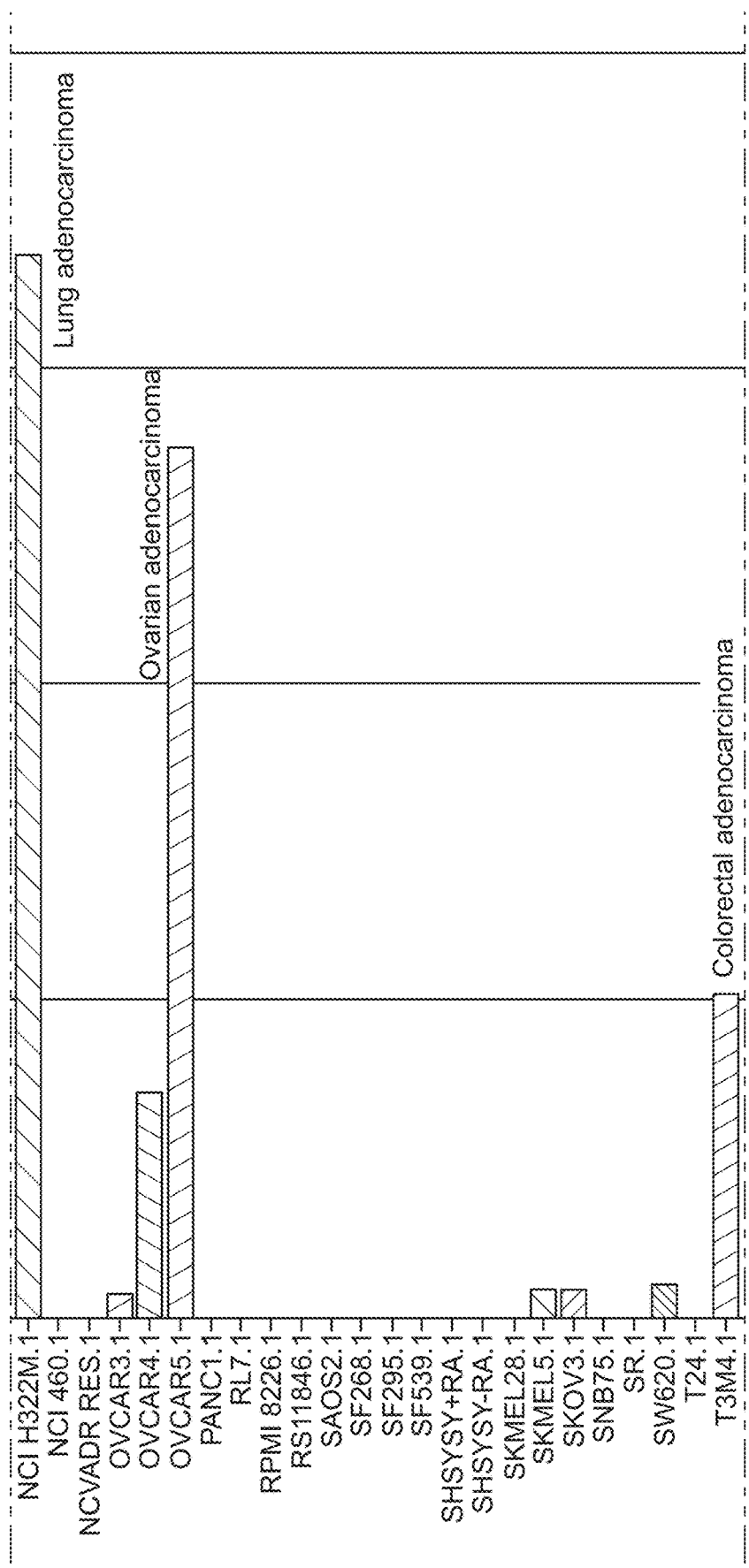

Analysis of the National Cancer Institute's NCI-60 U133A microarray dataset, available through the Biogps portal, demonstrates E-cadherin overexpression in multiple cancer cell lines (microarray data analysis shown in FIG. 10). In analysis of The Cancer Genome Atlas (TCGA) RNAseq data, E-cadherin's expression in tumor biopsy samples is consistently higher than that of the PD-1 ligand PD-L1 (FIG. 5). Accordingly, lung, breast, colon, prostate, melanoma, and ovarian cancers are particularly attractive targets for therapies according to the present invention.

Example 5: Production of Antibodies that Bind Human KLRG1

Antibodies that bind to the extracellular portion of KLRG1 and neutralize or compete with its ligands E-cadherin/N-cadherin/P-cadherin can be produced by several techniques including but not limited to: mouse hybridoma technology, phage display, yeast display, retrocyte display, humanized mouse technology, ribosome display. Other and additional methods are known in the art and can be developed in connection with the application of the present invention.

For example, mouse hybridoma technology can be used to generate antibodies that bind to KLRG1 and neutralize binding of E-cadherin (or deplete KLRG1 expressing cells). Mouse strains commonly used for antibody generation can be used, for example: Balb/c or SJL strains. Multiple mice can be injected repeatedly at 2 weeks intervals with antigen to produce an immune response. Several forms of the antigen can be injected either alone or in combination and with the addition of adjuvants such as KLH (keyhole limpet hemocyanin) known to enhance the immune response of the host to foreign antigens. Antigens can be in the form of purified recombinant KLRG1, cDNA coding for KLRG1, cells expressing KLRG1 on their surface or peptides derived from the sequence of KLRG1.

After every administration of antigens to the mice, the immune response against KLRG1 can be monitored by ELISA titer. The ELISA can be carried out by first immobilizing recombinant KLRG1 on suitable ELISA microtiter plates. After 12 hour incubation, the plates can be washed with phosphate saline and blocked with 1% solution of BSA in phosphate buffered saline. Sera derived from immunized mice can be serially diluted in phosphate buffered saline and allowed to interact with the surface bound antigen in the microtiter plates. Excess sera can be washed away and the amount of binding can be visualized using standard techniques such as addition of anti-mouse antibody conjugated to HRP. Mice can be boosted with antigen until a sufficiently high level of signal can be detected in their serum at which point the spleen can be removed from the mice. Splenocytes derived from immunized mice can be fused with myeloma derived (SP2/0) using standard protocols in use in the field. The resulting hybridoma cells can express and secrete antibodies that can be tested for binding to recombinant KLRG1 using ELISA and to cell expressed KLRG1 using FACS. Hybridoma cell lines that produce antibodies with desired binding characteristics can be sub-cloned and the variable regions of the antibody sequenced. Recombinant antibodies using these variable mouse regions and human constant regions can produced by standard techniques, and can be evaluated in functional assays (e.g., for binding, neutralization activity).

Example 6: An Assay for the Identification of Antibodies that Neutralize Human KLRG1 Binding to E-Cadherin KLRG1 binds to E-cadherin with a relatively low affinity (KD measured to be on the order of 200 μM). Due to this low binding affinity, a kinetic binding assay, for example as described in Example 21, can be used to measure the ability of an antibody that binds to KLRG1 to compete with E-cadherin interaction. The assays can use a kinetic binding parameter as measured by OCTET (ForteBio, Inc.) to establish whether antibodies that interact with KLRG1 prevent binding of E-cadherin. The assay can immobilize recombinant KLRG1 extracellular domain to an octet biosensor, either by direct absorption or by using an affinity tag such as anti-His or anti-FLAG. The loaded sensor can then be exposed to a solution of containing the antibody of interest and, if a binding even is measured by the instrument, the antibody under examination can be considered a "binder" and retained for further research and development. Otherwise the antibody can be considered a "non-binder" and discarded.

Example 7: Anti-KLRG1 Neutralizing Antibodies can Result in Increased Ex Vivo Human CD8$^+$ and NK Cell Proliferation CD8$^+$ T cells and NK cells isolated from human PBMCs can be labeled with Carboxyfluorescein succinimidyl ester (CFSE) and stimulated with plate coated anti-CD3 (OKT3 clone) and irradiated APCs. Proliferation in response to presence of anti-KLRG1 antibodies can be measured at day 3 and day 6 by FACS by monitoring the proportion of T cells and NK cells with dilution of CSFE staining. In various embodiments, anti-KLRG1 treated cells can proliferate at a faster rate compared to control IgG treated cells.

Example 8: Anti-KLRG1 Neutralizing Antibodies can Result in Ex Vivo Human CD8$^+$ and NK Cell Proliferation in Synergy with Other Check Point Inhibitors Such as Anti-PD-1 or Anti-PD-L1

CD8$^+$ T cells and NK cells isolated from human PBMCs can be labeled with Carboxyfluorescein succinimidyl ester (CFSE) and stimulated with plate coated anti-CD3 (OKT3 clone) and irradiated APCs. Proliferation in response to presence of anti-PD1 antibodies or anti-PDL1 can be measured at day 3 and day 6 by FACS by monitoring the proliferation of T cells and NK cells by dilution of CSFE staining. A second treatment with anti-KLRG1 antibodies can then be performed to measure further expansion of T-cells. Proliferation in response to anti-KLRG1 antibodies or control can be measured at day 3 and day 6 by FACS by monitoring the proliferation of T cells and NK cells by dilution of CSFE staining. In various embodiments, anti-KLRG1 treatment after PD-1/PD-L1 blockade can result in further enhancement of proliferation when compared to anti-PD-1 or anti-PD-L1 treatment alone.

Example 9: Anti-KLRG1 Neutralizing Antibodies can Synergize with Other Check Point Inhibitors, Such as Anti-PD-1 and Anti-PD-L1 Antibodies, Resulting in Increased Ex Vivo Human CD8$^+$ and NK Cell Cytokine Secretion CD8$^+$ T cells and NK cells can be isolated from human PBMCs, stimulated with plate coated anti-CD3 (OKT3 clone), irradiated antigen presenting cells (APCs), and treated with anti-KLRG1 antibodies, in the presence of other check point inhibitors such as anti-PD1 or anti-PD-L1 or IgG control antibody. Secretion of pro-inflammatory cytokines such as IL2 and IFN-gamma, can be measured in the media 3 and 6 days post stimulation by ELISA or similar technique. In various embodiments, treatment with the combination of anti-KLRG1 and either anti-PD-1 or anti-PD-L1 can result in increased secretion of pro-inflammatory cytokines compared to cells treated with either of the antibodies alone.

Example 10: Melanoma

Figure 11:
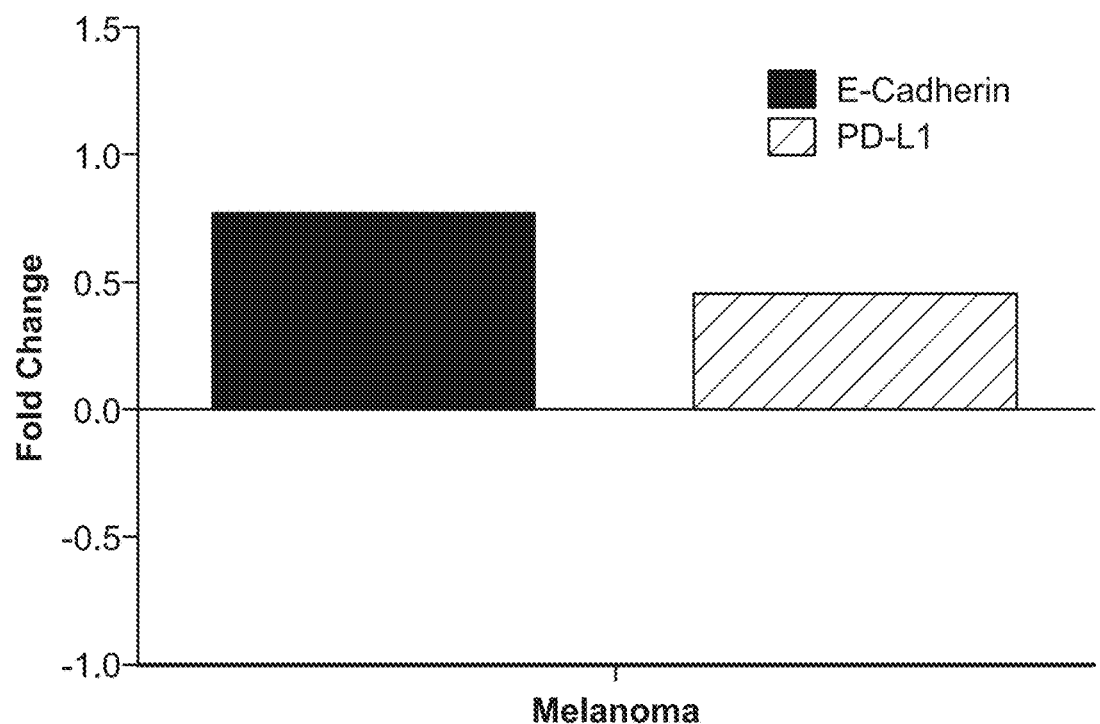
FIG. 11 shows the fold-change of E-cadherin and PD-L1 in melanoma TCGA RNAseq data in comparison to normal skin tissue.

FIG. 11 shows the fold-change of E-cadherin and PD-L1 in melanoma TCGA RNAseq data in comparison to normal skin tissue from GTEX data (Genotype-Tissue Expression, at www.gtexportal.org/). Expression of E-cadherin is high in melanoma (fold-change 0.77), and is higher than that of PD-L1 (fold-change 0.45). Accordingly, melanoma is a particularly attractive target for therapies according to the present invention.

Example 11: Lung Cancer

Figure 12:
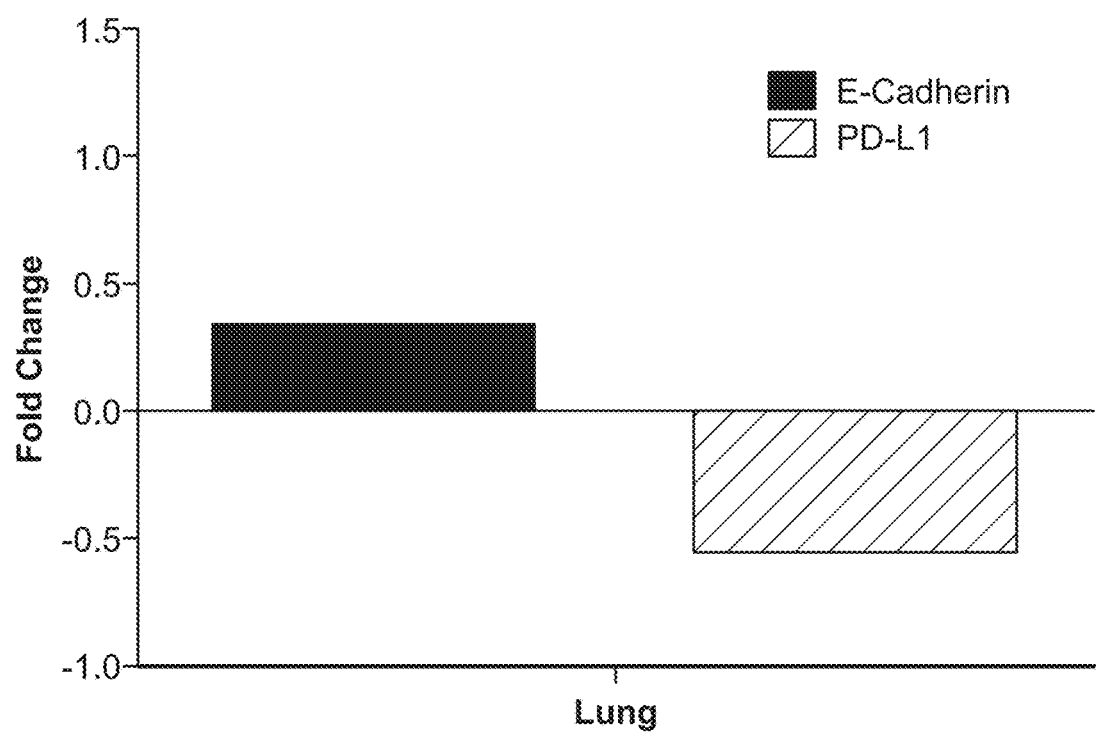
FIG. 12 shows the fold-change of E-cadherin and PD-L1 in lung cancer TCGA RNAseq data in comparison to normal lung tissue.

FIG. 12 shows the fold-change of E-cadherin and PD-L1 in lung cancer TCGA RNAseq data in comparison to normal lung tissue from GTEX data. Expression of E-cadherin is high in lung cancer (fold-change 0.31), and is higher than that of PD-L1 (fold-change −0.57). Accordingly, lung cancer is a particularly attractive target for therapies according to the present invention.

Example 12: Pancreatic Cancer

Figure 13:
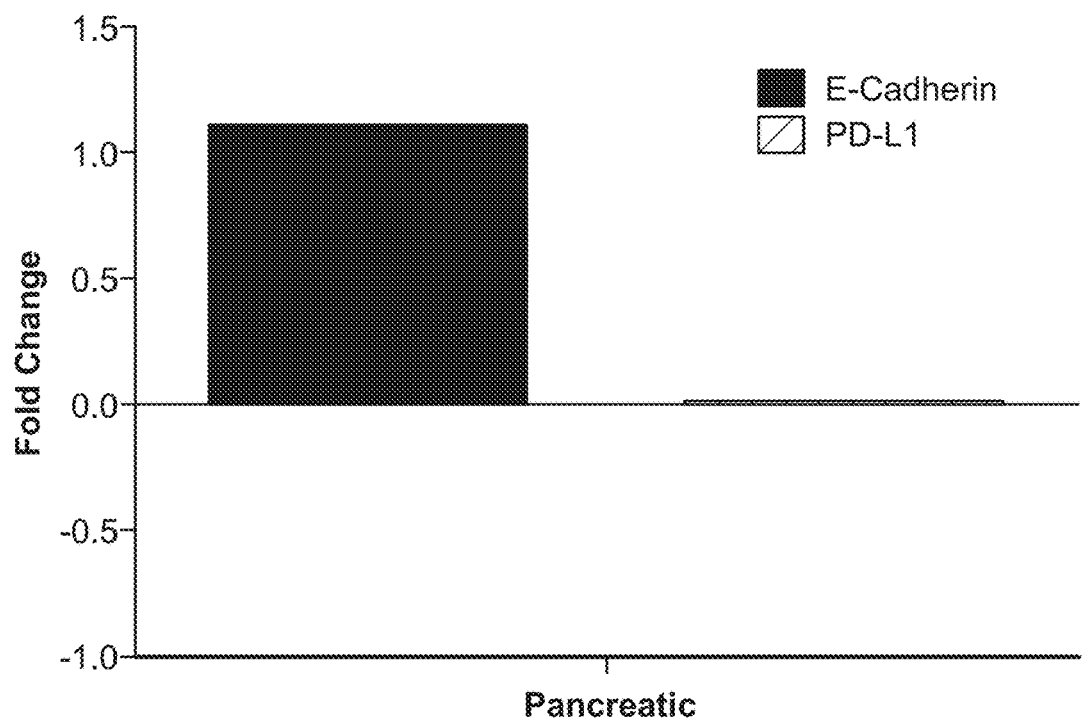
FIG. 13 shows the fold-change of E-cadherin and PD-L1 in pancreatic cancer TCGA RNAseq data in comparison to normal pancreatic tissue.

FIG. 13 shows the fold-change of E-cadherin and PD-L1 in pancreatic cancer TCGA RNAseq data in comparison to normal pancreatic tissue from GTEX data. Expression of E-cadherin is high in pancreatic cancer (fold-change 1.10), and is higher than that of PD-L1 (fold-change 0.01). Accordingly, prostate cancer is a particularly attractive target for therapies according to the present invention.

Example 13: Glioma

Figure 14:
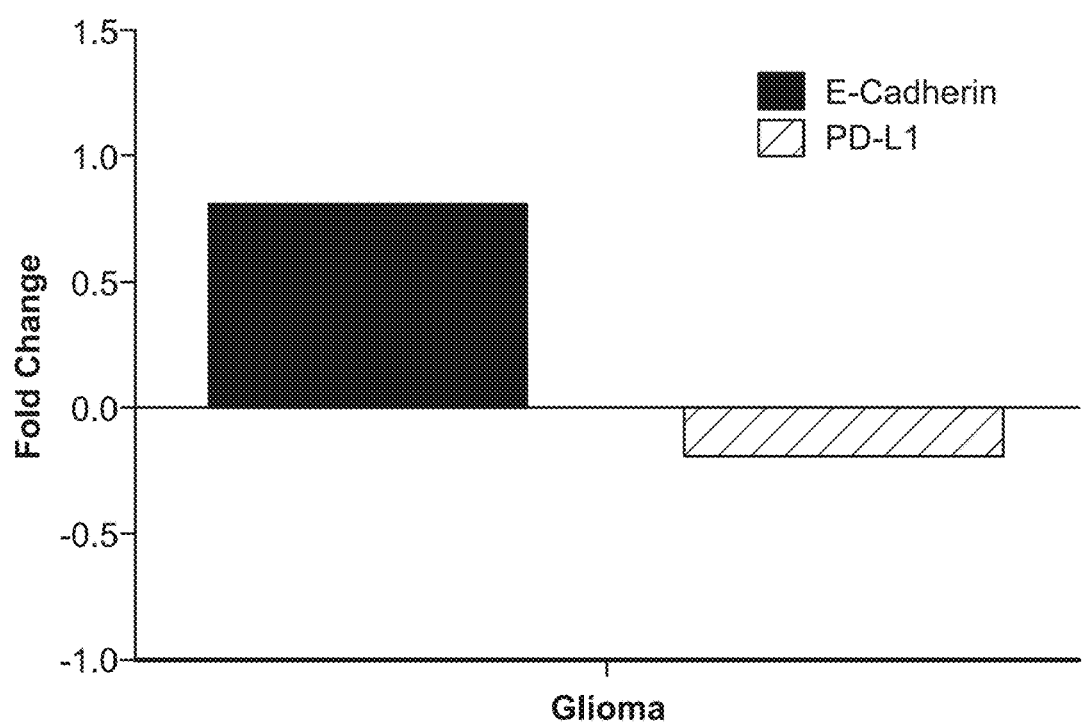
FIG. 14 shows the fold-change of E-cadherin and PD-L1 in glioma TCGA RNAseq data in comparison to normal brain tissue.

FIG. 14 shows the fold-change of E-cadherin and PD-L1 in glioma TCGA RNAseq data in comparison to normal brain tissue from GTEX data. Expression of E-cadherin is high in glioma (fold-change 0.80), and is higher than that of PD-L1 (fold-change −0.19). Accordingly, brain cancer (e.g., glioma) is a particularly attractive target for therapies according to the present invention.

Example 14: Breast Cancer

Figure 15:
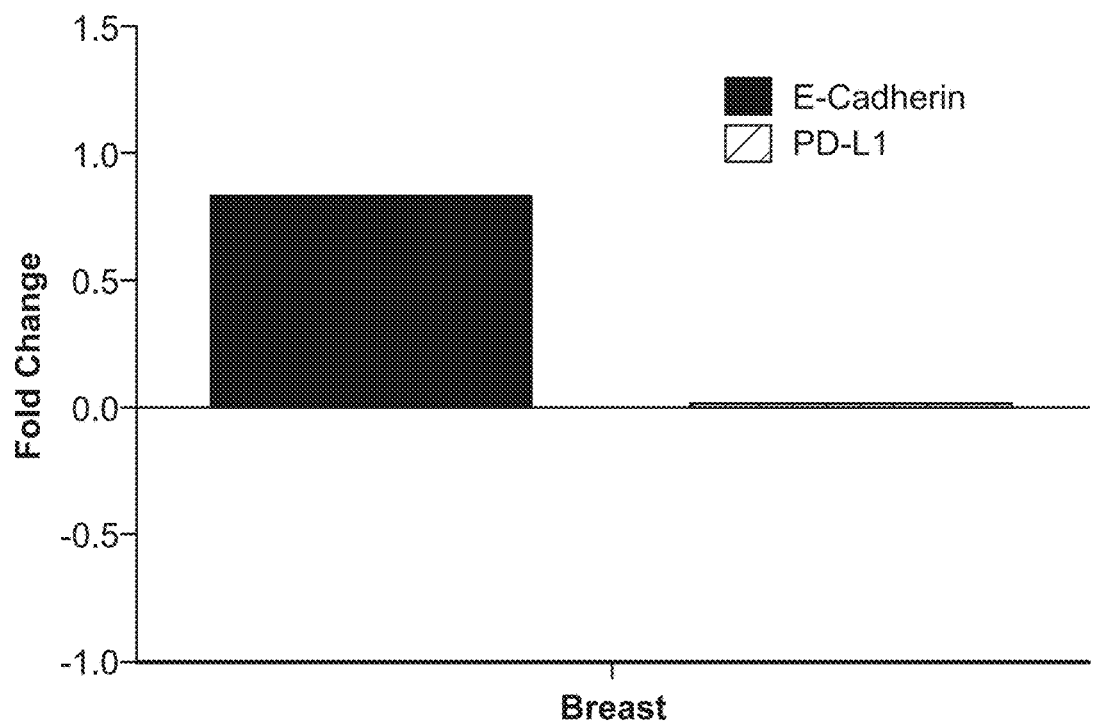
FIG. 15 shows the fold-change of E-cadherin and PD-L1 in breast cancer TCGA RNAseq data in comparison to normal breast tissue.

FIG. 15 shows the fold-change of E-cadherin and PD-L1 in breast cancer TCGA RNAseq data in comparison to normal breast tissue from GTEX data. Expression of E-cadherin is high in breast cancer (fold-change 0.84), and is higher than that of PD-L1 (fold-change 0.01). Accordingly, breast cancer is a particularly attractive target for therapies according to the present invention.

Example 15: Ovarian Cancer

Figure 16:
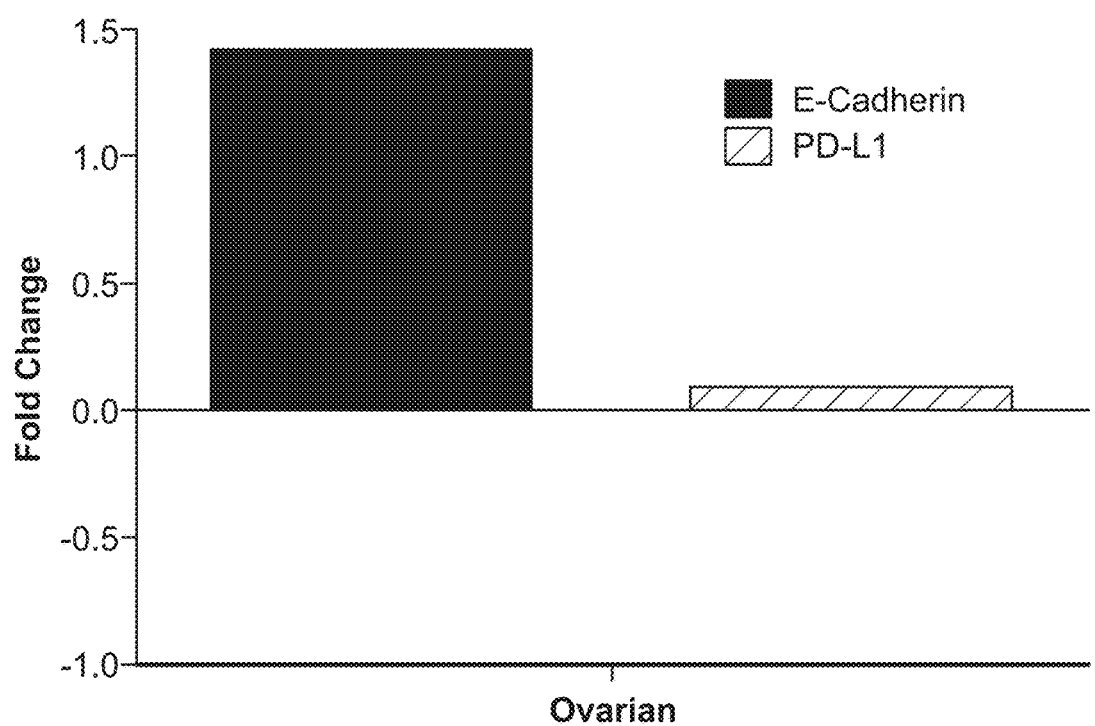
FIG. 16 shows the fold-change of E-cadherin and PD-L1 in TCGA ovarian cancer RNAseq data in comparison to normal ovarian tissue.

FIG. 16 shows the fold-change of E-cadherin and PD-L1 in TCGA ovarian cancer RNAseq data in comparison to normal ovarian tissue from GTEX data. Expression of E-cadherin is high in ovarian cancer (fold-change 1.41), and is higher than that of PD-L1 (fold-change 0.08). Accordingly, ovarian cancer is a particularly attractive target for therapies according to the present invention.

Example 16: Melanoma

Figure 17A:
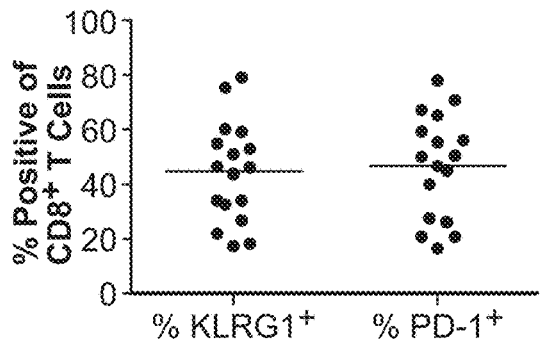
FIGS. 17A-D show that KLRG1 is expressed by a large proportion of melanoma infiltrating T cells, including PD-1 negative T cells.
Figure 17B:
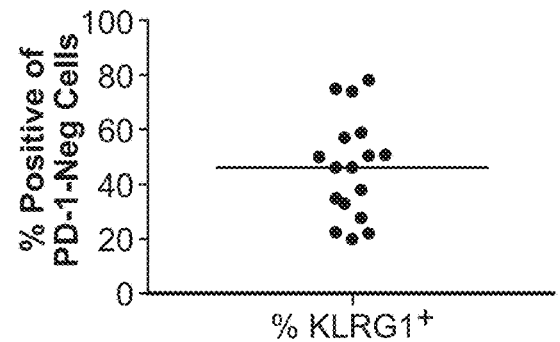
Figure 17C:
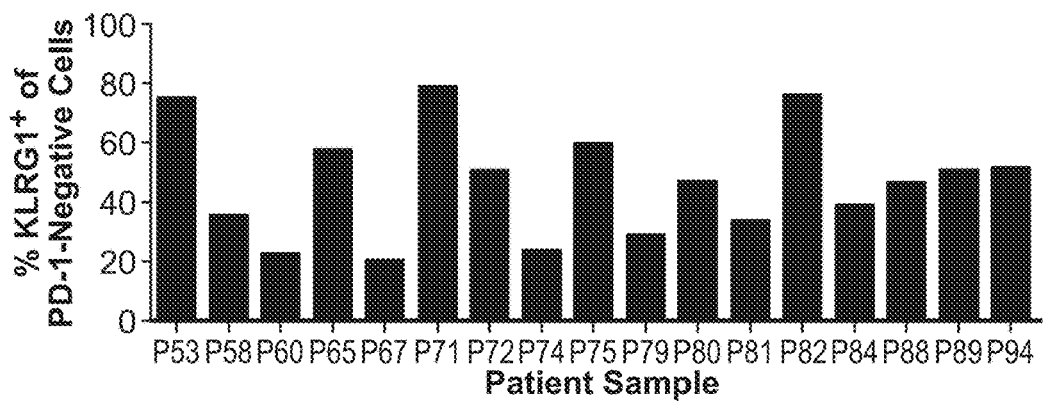
Figure 17D:
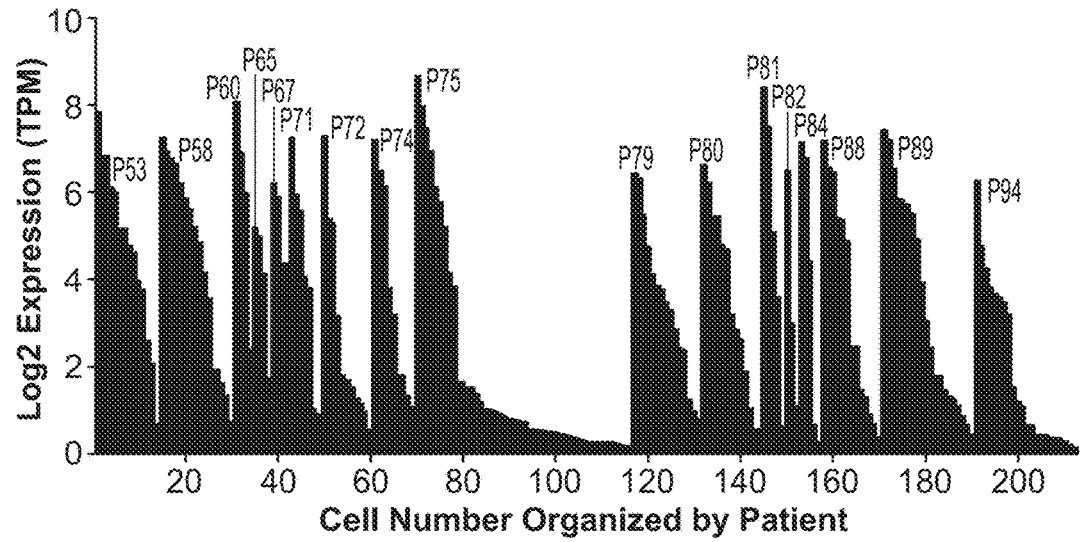
Figure 18A:
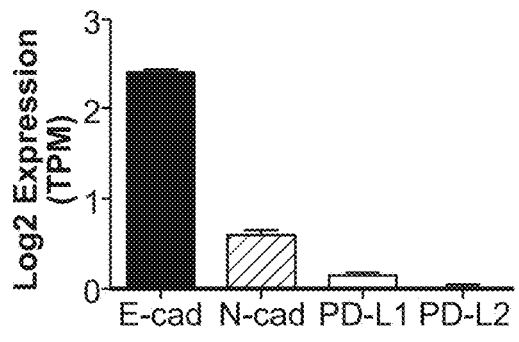
FIGS. 18A-D show KLRG1 ligands E-cadherin and N-cadherin are much more highly expressed by malignant melanoma cells than PD-1 ligands PD-L1 and PD-L2.
Figure 18B:
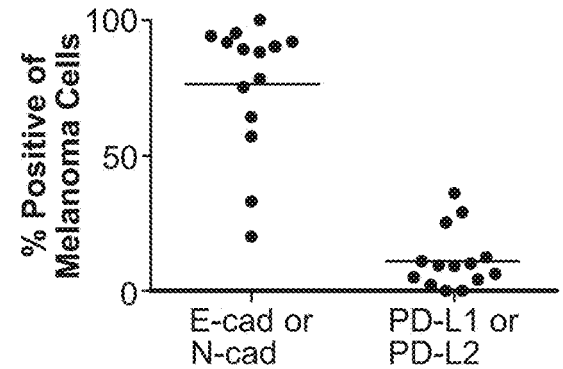
Figure 18C:
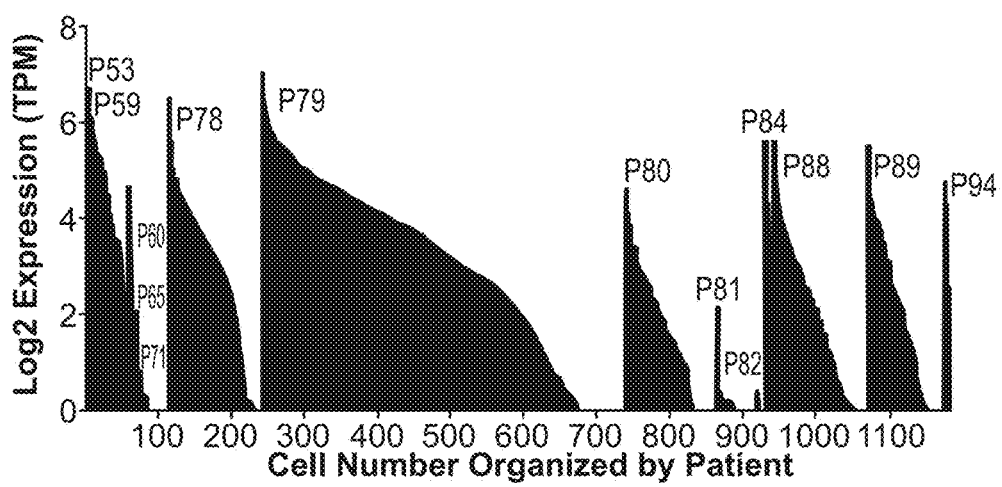
Figure 18D:
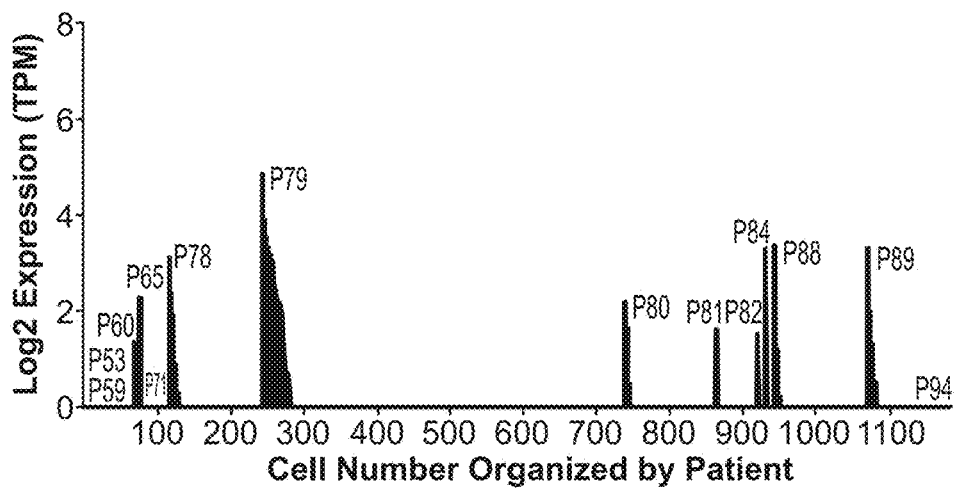

KLRG1 is expressed by a substantial proportion of CD8$^+$ T cells within melanoma patient biopsies (RNA-seq data GEO database, accession number GSE72056). Specifically, the mean percentage of CD8$^+$ T cells that express KLRG1 (across 17 patient melanoma biopsy samples) is 44% and that express PD-1 is 47% (FIG. 17A, KLRG1 and PD-1 CD8$^+$ expression by melanoma patient sample), similar and not significantly different proportions. Substantial number of PD-1-negative CD8$^+$ T cells are KLRG1$^+$, so that targeting KLRG1 can affect a population of cells unaffected by targeting PD-1 with existing drugs such as nivolumab or pembrolizumab. Specifically, across 17 patient melanoma biopsy samples, a mean of 46% (range 20% to 78%) of PD-1 negative CD8$^+$ T cells express KLRG1 (FIG. 17B, KLRG1 expression in PD-1-negative CD8$^+$ T cells and FIG. 17C, KLRG1$^+$ PD-1-negative CD8$^+$ cells by melanoma patient sample). Expression levels of KLRG1 are high (up to 6-8 transcripts per million bases) in many of these KLRG1$^+$ PD-1-negative CD8$^+$ cells (FIG. 17D, KLRG1 expression in PD-1-negative CD8$^+$ T cells from 17 patient melanoma biopsy samples). Additionally, analysis of this single cell dataset for expression of relevant ligands by malignant melanoma cells demonstrates that KLRG1's ligand, E-cadherin, is expressed in a substantial proportion of melanoma malignant cells (a mean of 76% across 14 patients) and a far greater proportion than the PD-1 ligand PD-L1 (a mean of 11%) (FIG. 18A-D). Accordingly, melanoma is a particularly attractive target for therapies according to the present invention.

Example 17: Summary of Relative Expression in Cancer Tissues Versus Normal Matching Tissue for E-Cadherin and for PD-L1

Figure 19:
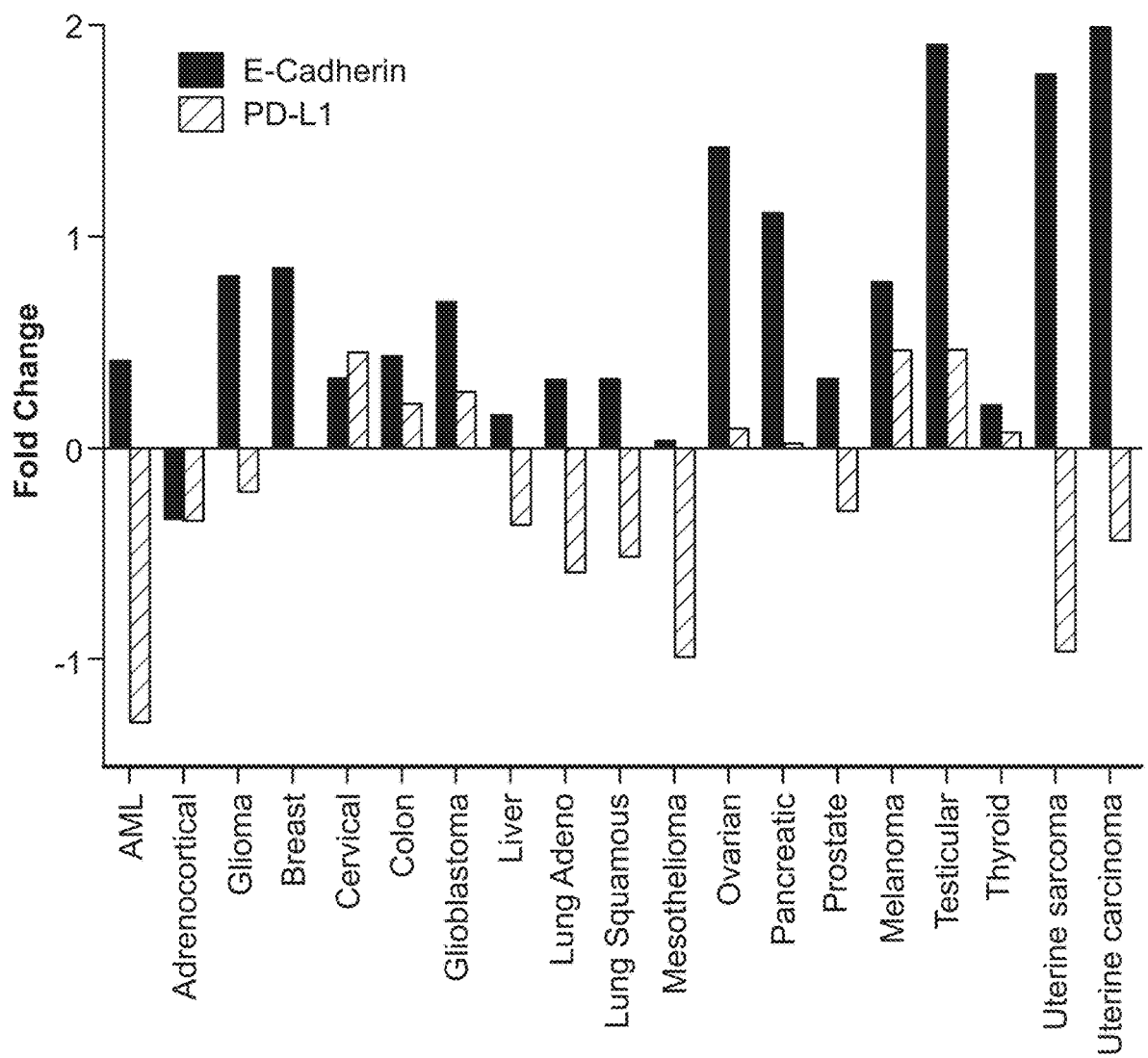
FIG. 19 shows a summary of relative expression in cancer tissues versus normal matching tissue for E-cadherin and for PD-L1.

FIG. 19 shows a summary of relative expression in cancer tissues versus normal matching tissue for E-cadherin and for PD-L1. These data reflect the data in FIGS. 11-16, which are presented here in a single figure for comparison.

Example 18: Downregulation of KLRG1 Gene Expression by RNAi

Human peripheral blood mononuclear cells ("PBMC") can be isolated and treated with RNAi designed to specifically downregulate the expression of KLRG1 gene by targeting the coding mRNA. RNAi constructs can be designed applying well know techniques (e.g., as described in Brown et al. (2002) RNA interference in mammalian cell culture: design, execution, and analysis of the siRNA effect. Ambion TechNotes 9(1): 3-5.). Starting from the mRNA for the target of interest (e.g., KLRG1 mRNA SEQ ID NO:7) a sequence corresponding to 20 base pairs is selected and constitutes the "sense" region of the construct. The RNAi construct generally includes a 5 prime "sense" sequence followed by a "loop" region and by an "anti-sense" sequence complementary to the sense sequence. The construct can be synthetized and cloned into a delivery retroviral vector. PBMCs isolated from healthy volunteers can be infected with viral particles carrying the RNAi coding vector and their proliferative capacity can be tested by stimulation with anti-CD3 antibody (OKT3). PBMCs treated with such RNAi can display a higher level of proliferation compared with untreated PBMCs.

Example 18: Melanoma

Figure 20:
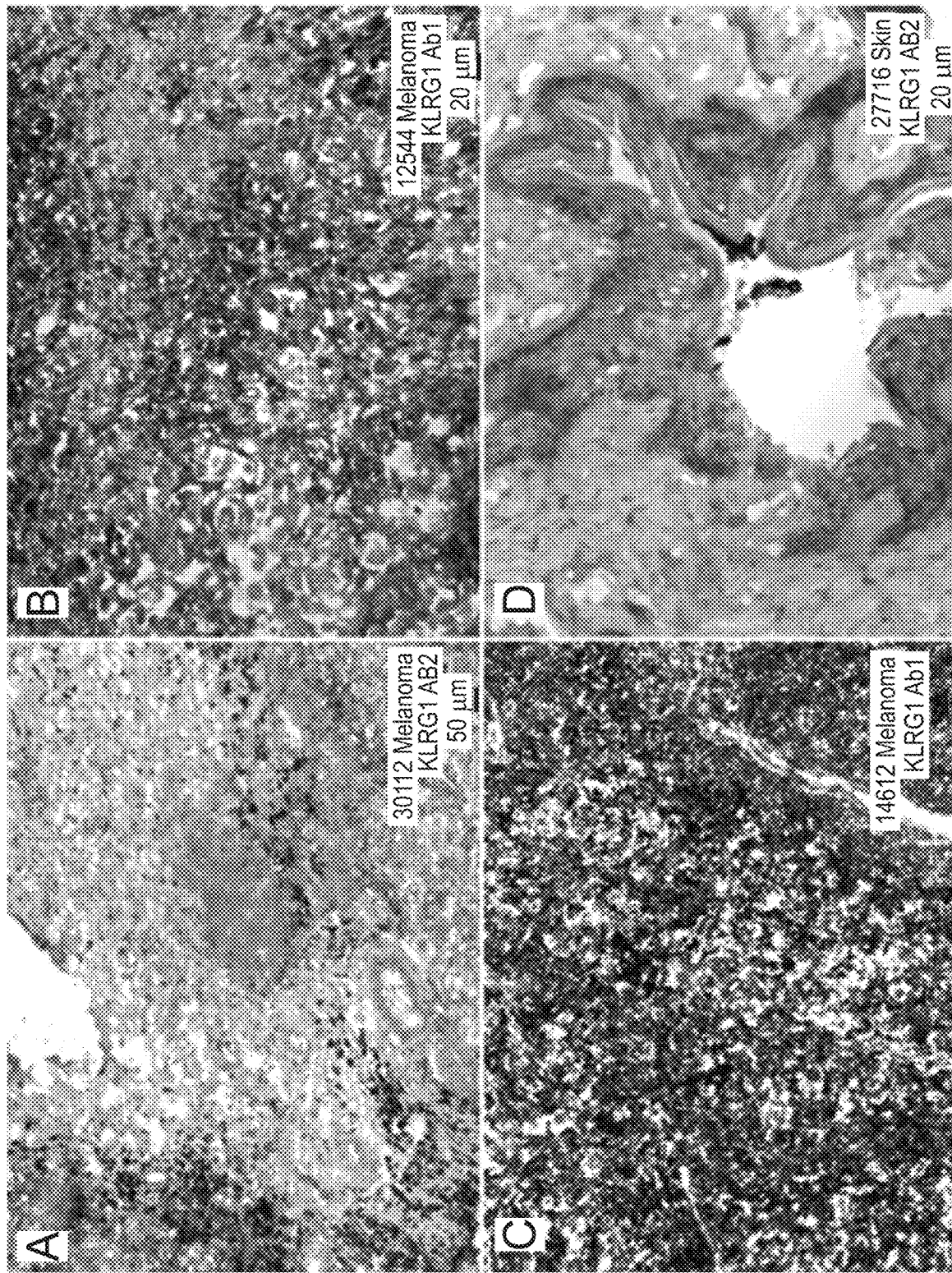
FIG. 20 shows KLRG1$^+$ cells infiltrating melanoma tumors in example patients.

Immunohistochemistry of human melanoma biopsies from 3 patients demonstrates abundant KLRG1$^+$ cells infiltrating tumor (A-C) but absence of KLRG1$^+$ cells in normal skin (D) (FIG. 20). The presence of KLRG1$^+$ cells in tumor tissue render melanoma a particularly attractive target for therapies according to the present invention.

Example 19: Renal Cell Carcinoma

Figure 21:
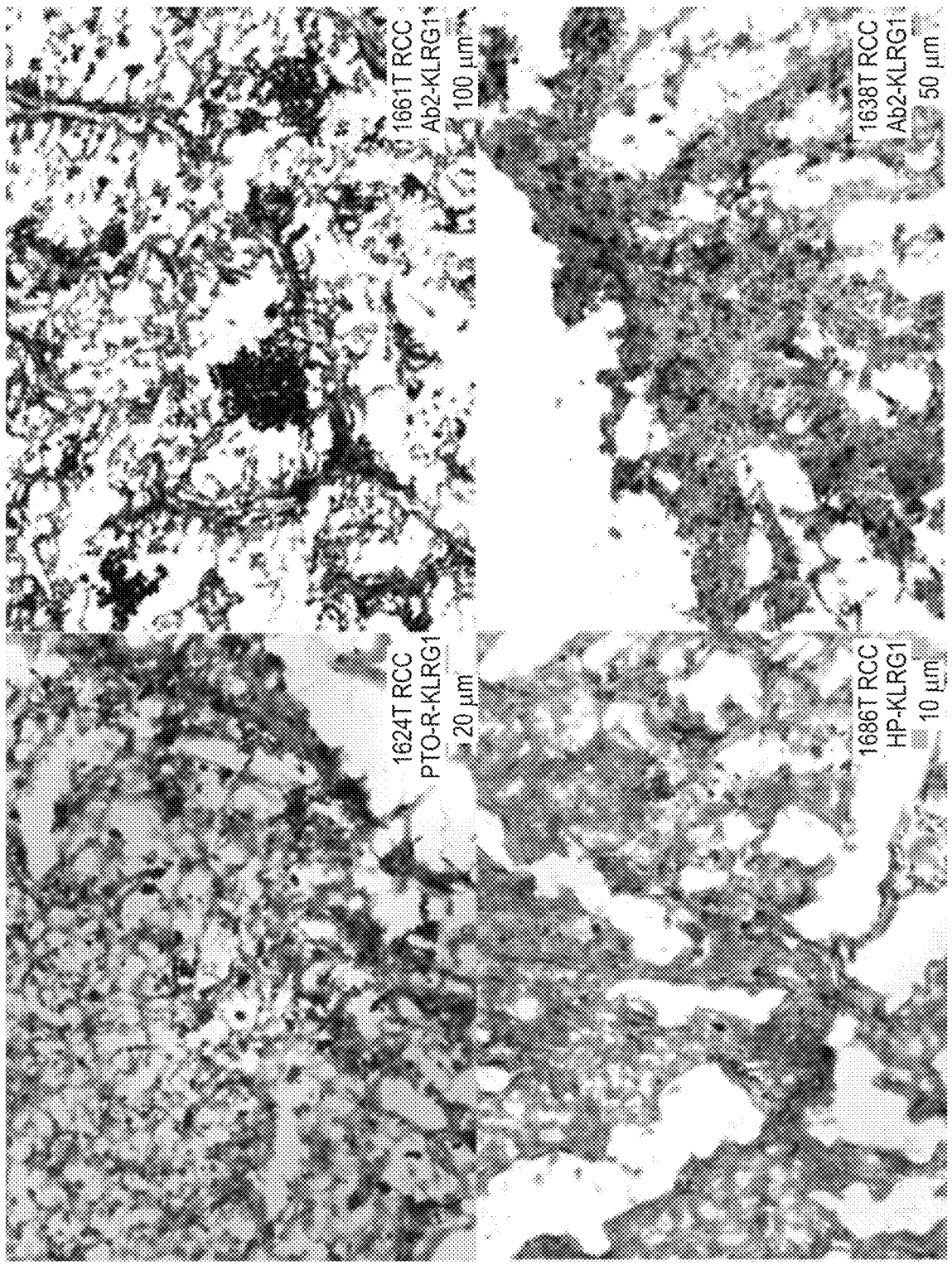
FIG. 21 shows KLRG1$^+$ cells infiltrating renal cell carcinoma tumors in example patients.

Immunohistochemistry of human renal cell carcinoma biopsies from 4 patients demonstrates abundant KLRG1$^+$ cells infiltrating tumor (FIG. 21). The presence of KLRG1$^+$ cells in tumor tissue render renal cell carcinoma a particularly attractive target for therapies according to the present invention.

Example 20: Non-Small Cell Lung Cancer

Figure 22:
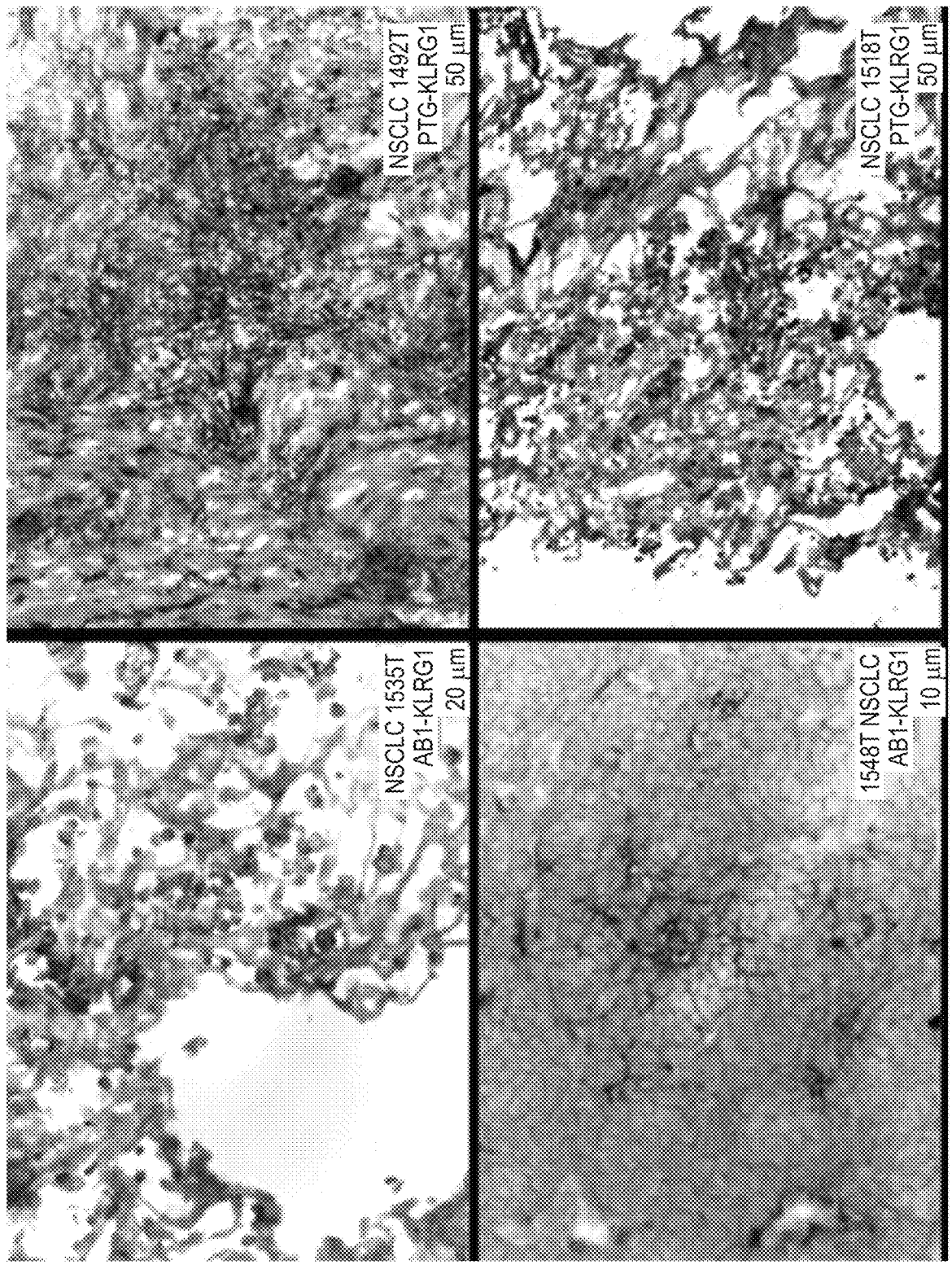
FIG. 22 shows KLRG1$^+$ cells infiltrating non-small cell lung cancer tumors in example patients.

Immunohistochemistry of human non-small cell lung cancer biopsies from 4 patients demonstrates abundant KLRG1$^+$ cells infiltrating tumor (FIG. 22). The presence of KLRG1$^+$ cells in tumor tissue render non-small cell lung cancer a particularly attractive target for therapies according to the present invention.

Example 21: Binding of Recombinant Human E-Cadherin to Human KLRG1, and Detection of Antibodies with Neutralizing Activity An ELISA based KLRG1/E-cadherin competition assay was developed to measure KLRG1/E-cadherin binding as well as neutralization of KLRG1/E-cadherin binding.

E-Cadherin/KLRG1 Binding

Further to Example 6, binding of h (human) KLRG1 to h (human) E-cadherin can be detected by ELISA. The ELISA detects the binding of E-cadherin to plate-coated KLRG1, and defines a neutralizing antibody as having the effect of reducing the E-cadherin binding to KLRG1 in a dose dependent manner.

Figure 23:
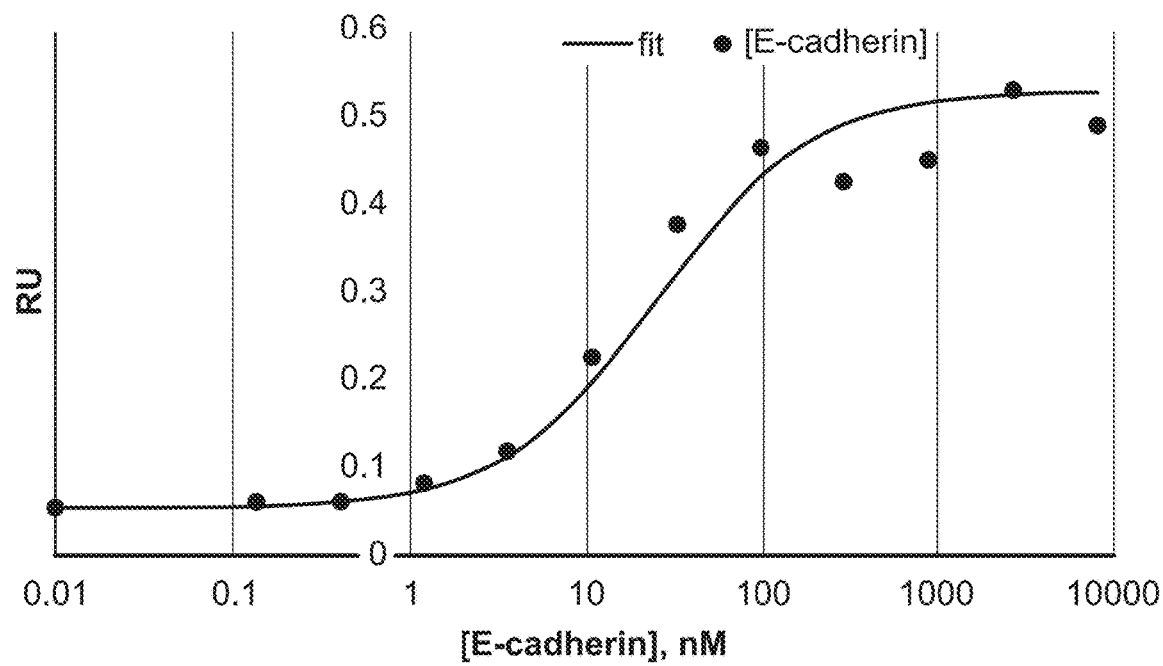
FIG. 23 presents the results of soluble hE-cadherin binding to plate-coated hKLRG1.

FIG. 23 presents the results of soluble hE-cadherin binding to plate-coated hKLRG1. From this curve, EC50 and EC80 were calculated to be 25 and 100 nM, respectively. Optimal KLRG1/E-cadherin interaction was observed in buffer with the following composition: 1×PBS, 1% BSA, 2% Dry Milk, 0.05% Tween.

Anti-KLRG1 Chimeric Antibodies

Three murine anti-KLRG1 antibodies, one of which is commercially available, were used to produce mouse-human chimeric antibodies (labeled HYB01, HYB02, and HYB03). The three chimeric antibodies were compared with respect to neutralizing activity and hKLRG1 binding.

Neutralization of hE-Cadherin/hKLRG1 Binding

Figure 24:
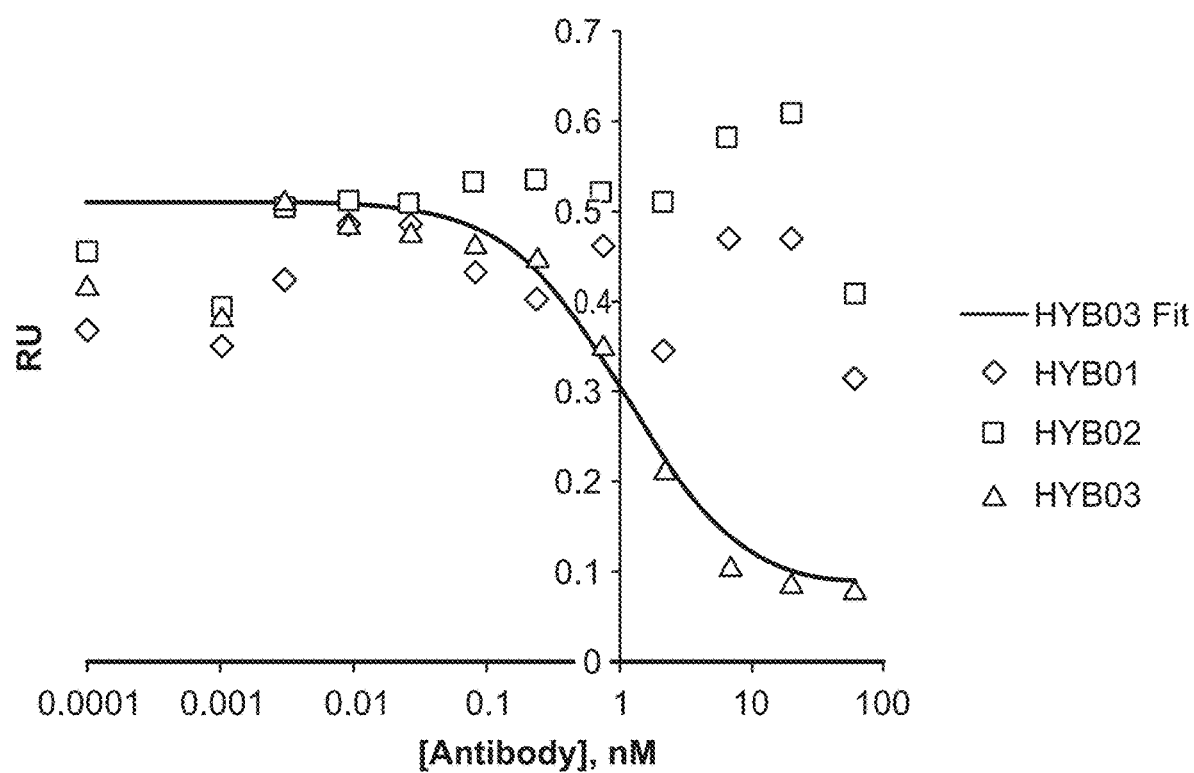
FIG. 24 presents the results of the three chimeric antibodies tested for neutralizing hE-cadherin/hKLRG1 binding, with only one chimeric antibody demonstrating neutralizing activity.

FIG. 24 presents the results of the three mouse-human chimeric antibodies neutralizing hE-cadherin/hKLRG1 binding. The concentration of soluble E-cadherin was fixed at the EC80 value of 100 nM, while the concentration of chimeric antibodies was varied. Chimeric antibody HYB03 shows a dose dependent neutralization (IC50 of 1.1 nM). Chimeric antibodies HYB01 and HYB02 show effectively no dose dependent neutralization (IC50 NA).

Chimeric Antibody/hKLRG1 Binding

Figure 25:
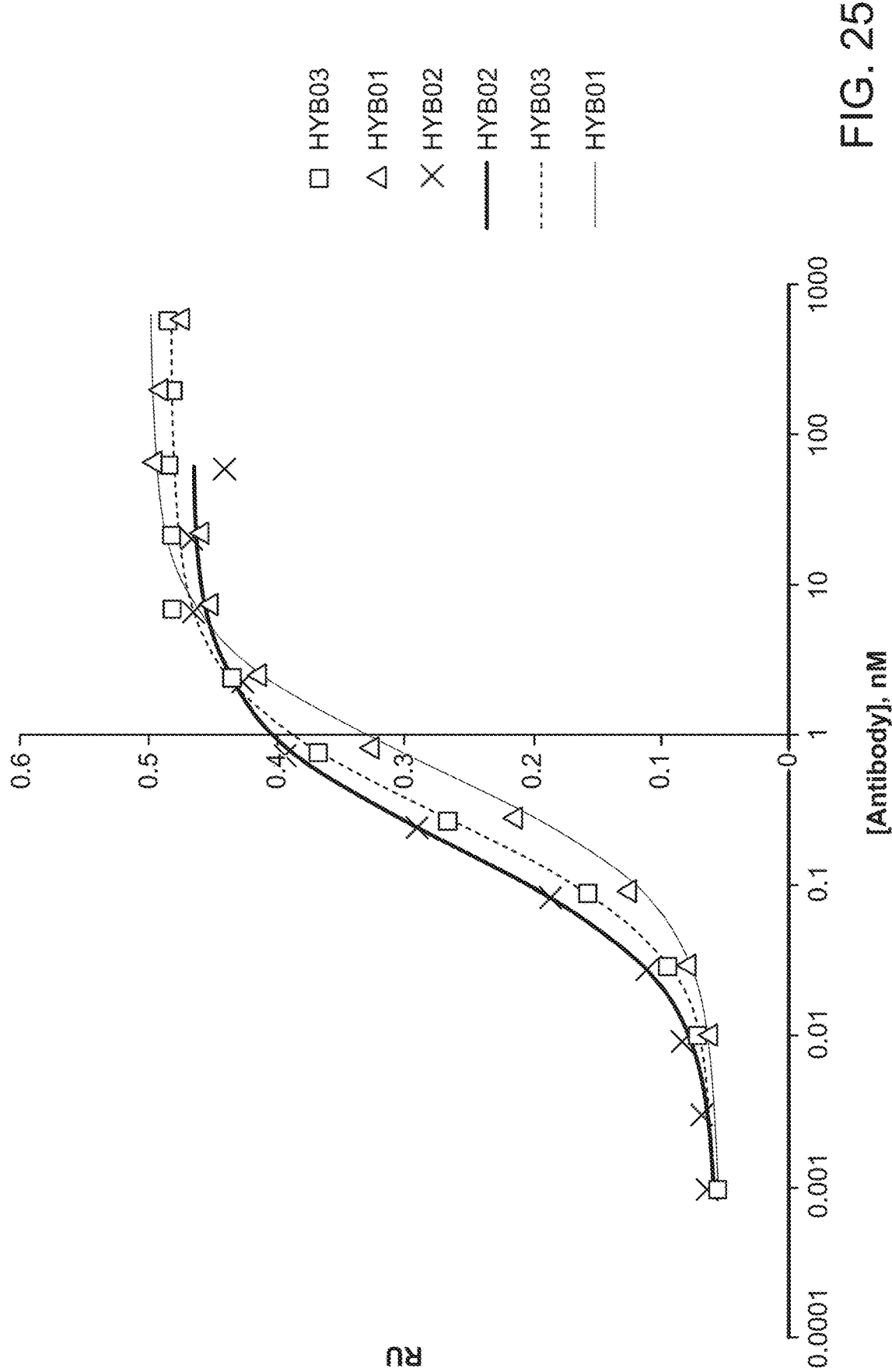
FIG. 25 presents the results of the three chimeric antibodies binding to plate coated KLRG1 in a dose dependent manner.

FIG. 25 presents the results of the three mouse-human chimeric antibodies binding to plate coated KLRG1 in a dose dependent manner, as determined by ELISA. HYB01 has an EC50 of 0.6 nM, HYB02 has an EC50 of 0.18 nM, and HYB03 has an EC50 of 0.28 nM.

Summary

Although all three tested mouse-human chimeric antibodies (HYB01, HYB02, and HYB03) bind hKLRG1 in a dose dependent manner, only one (HYB03) also exhibits dose dependent neutralization. The neutralization assay is thus capable of distinguishing neutralizing antibodies from those that are merely KLRG1 binding.

REFERENCES

Akbar A N, Henson S M. Are senescence and exhaustion intertwined or unrelated processes that compromise immunity? Nat Rev Immunol. 2011; 11(4):289-95.

Apetoh L, Smyth M J, Drake C G, Abastado J P, Apte R N, Ayyoub M, et al. Consensus nomenclature for CD8$^+$ T cell phenotypes in cancer. Oncoimmunology. 2015; 4(4): e998538.

Attig S, Hennenlotter J, Pawelec G, Klein G, Koch S D, Pircher H, et al. Simultaneous infiltration of polyfunctional effector and suppressor T cells into renal cell carcinomas. Cancer Res. 2009; 69(21):8412-9.

Blackburn S D, Shin H, Haining W N, Zou T, Workman C J, Polley A, et al. Coregulation of CD8$^+$ T cell exhaustion by multiple inhibitory receptors during chronic viral infection. Nat Immunol. 2009; 10(1):29-37.

Brunner S M, Rubner C, Kesselring R, Martin M, Griesshammer E, Ruemmele P, et al. Tumor-infiltrating, interleukin-33-producing effector-memory CD8$^+$ T cells in resected hepatocellular carcinoma prolong patient survival. Hepatology. 2015; 61(6):1957-67.

Cyktor J C, Carruthers B, Stromberg P, Flano E, Pircher H, Turner J. Killer cell lectin-like receptor G1 deficiency significantly enhances survival after *Mycobacterium tuberculosis* infection. Infect Immun. 2013; 81(4):1090-9.

Grundemann C, Schwartzkopff S, Koschella M, Schweier O, Peters C, Voehringer D, et al. The N K receptor KLRG1 is dispensable for virus-induced N K and CD8$^+$ T-cell differentiation and function in vivo. Eur J Immunol. 2010; 40(5):1303-14.

Guthmann M D, Tal M, Pecht I. A new member of the C-type lectin family is a modulator of the mast cell secretory response. Int Arch Allergy Immunol. 1995; 107(1-3):82-6.

Henson S M, Franzese O, Macaulay R, Libri V, Azevedo R I, Kiani-Alikhan S, et al. KLRG1 signaling induces defective Akt (ser473) phosphorylation and proliferative dysfunction of highly differentiated CD8$^+$ T cells. Blood. 2009; 113(26):6619-28.

Henson S M, Macaulay R, Franzese O, Akbar A N. Reversal of functional defects in highly differentiated young and old CD8$^+$ T cells by PDL blockade. Immunology. 2012; 135(4):355-63.

Hofmann M, Schweier O, Pircher H. Different inhibitory capacities of human and mouse KLRG1 are linked to distinct disulfide-mediated oligomerizations. Eur J Immunol. 2012; 42(9):2484-90.

Legat A, Speiser D E, Pircher H, Zehn D, Fuertes Marraco S A. Inhibitory Receptor Expression Depends More Dominantly on Differentiation and Activation than "Exhaustion" of Human CD8$^+$ T Cells. Front Immunol. 2013; 4:455.

Mahoney K M, Rennert P D, Freeman G J. Combination cancer immunotherapy and new immunomodulatory targets. Nature reviews Drug discovery. 2015; 14(8):561-84.

Melis L, Van Praet L, Pircher H, Venken K, Elewaut D. Senescence marker killer cell lectin-like receptor G1 (KLRG1) contributes to TNF-alpha production by interaction with its soluble E-cadherin ligand in chronically inflamed joints. Ann Rheum Dis. 2014; 73(6):1223-31.

Nishimura H, Nose M, Hiai H, Minato N, Honjo T. Development of lupus-like autoimmune diseases by disruption of the PD-1 gene encoding an ITIM motif-carrying immunoreceptor. Immunity. 1999; 11(2):141-51.

Shi L, Wang J M, Ren J P, Cheng Y Q, Ying R S, Wu X Y, et al. KLRG1 impairs CD4+ T cell responses via p16ink4a and p27kip1 pathways: role in hepatitis B vaccine failure in individuals with hepatitis C virus infection. J Immunol. 2014; 192(2):649-57.

Dimitri D, Benveniste O, Dubourg O, Maisonobe T, Eymard B, Amoura Z, et al. Shared blood and muscle CD8+ T-cell expansions in inclusion body myositis. Brain: a journal of neurology 2006; 129(Pt 4): 986-95.

Marcolino I, Przybylski G K, Koschella M, Schmidt C A, Voehringer D, Schlesier M, et al. Frequent expression of the natural killer cell receptor KLRG1 in human cord blood T cells: correlation with replicative history. Eur J Immunol 2004; 34(10): 2672-80.

Muntzing K, Lindberg C, Moslemi A R, Oldfors A. Inclusion body myositis: clonal expansions of muscle-infiltrating T cells persist over time. Scandinavian journal of immunology 2003; 58(2): 195-200.

Voehringer D, Koschella M, Pircher H. Lack of proliferative capacity of human effector and memory T cells expressing killer cell lectinlike receptor G1 (KLRG1). Blood 2002; 100(10): 3698-702.

The invention claimed is:

1. A method of treating a subject afflicted with cancer or infection comprising administering to said subject an effective amount of a binding agent, wherein said binding agent:
   (i) specifically binds killer cell lectin-like receptor G1 (KLRG1),
   (ii) disrupts KLRG1 signaling with a ligand of KLRG1 selected from the group consisting of E-cadherin, N-cadherin and R-cadherin, and
   (iii) activates CD8+ cytotoxic T cells,
   wherein the binding agent is an antibody, antigen binding fragment thereof, or antibody mimetic, or comprises an Fc-cadherin fusion protein,
   thereby treating said cancer or infection in said subject.

2. The method of claim 1, wherein the antibody or antigen binding fragment thereof, or antibody mimetic comprises a human or humanized antibody.

3. The method of claim 1, wherein said binding agent comprises:
   a. a full length antibody Fab portion that binds KLRG1;
   b. a fusion protein E-cadherin/Fc;
   c. a fusion protein R-cadherin/Fc;
   d. a fusion protein N-cadherin/Fc;
   e. a chimeric antigen receptor that binds KLRG1; or
   f. a multispecific antibody that binds KLRG1.

4. The method of claim 3, comprising the chimeric antigen receptor and wherein the chimeric antigen receptor comprises an antigen binding portion of a KLRG1 antibody grafted onto a T cell.

5. The method of claim 3, comprising a multispecific antibody and wherein the multispecific antibody comprises a bispecific or trispecific antibody.

6. The method of claim 1, wherein the KLRG1 is the extracellular domain of human KLRG1.

7. The method of claim 1, further comprising testing the subject for elevated KLRG1 expression on said CD8+ cytotoxic T cells.

8. The method of claim 1, wherein the subject has elevated cadherin expression.

9. The method of claim 1, wherein the antibody is monoclonal.

10. The method of claim 1, wherein said binding agent cross-reacts with the extracellular domains of human and cynomolgus KLRG1.

11. The method of claim 1, wherein said binding agent is not antibody clone 13F12F2, 14C2A07, SA231A2, 2F1, 13A2, or REA261.

12. The method of claim 1, wherein said binding agent is not a mouse antibody.

13. The method of claim 1, wherein said subject has cancer.

14. The method of claim 13, wherein said subject has elevated cadherin expression on cancer cells relative to corresponding non: transformed cells.

15. The method of claim 14, further comprising testing the subject for elevated cadherin expression on cancer cells relative to corresponding non-transformed cells.

16. The method of claim 1, further comprising administering to the subject an effective amount of a checkpoint modulator therapy.

17. The method of claim 16, wherein the checkpoint modulator therapy comprises an anti-PD-1, anti-PD-L1, or anti-CTLA-4 therapy.

18. The method of any of claims 1-13, further comprising administering to the subject an effective amount of a cancer vaccine therapy.

19. The method of claim 1 or claim 13, further comprising administering to the subject an effective amount of a cancer chemotherapy.

20. The method of claim 1 or claim 13, wherein the subject has cancer and has failed or has not responded to a prior cancer therapy.

21. The method of any of claims 1-13, wherein the subject has an epithelial cancer, and wherein said cancer expresses said ligand of KLRG1.

22. The method of any of claims 1-13, wherein the subject has a carcinoma, and wherein said carcinoma expresses said ligand of KLRG1.

23. The method of any of claims 1-13, wherein the subject has a cancer selected from the group consisting of: uveal melanoma, uterine carcinoma, uterine carcinosarcoma, thyroid carcinoma, thymoma, testicular germ cell tumor, melanoma, sarcoma, rectal adenocarcinoma, prostate cancer, pheochromocytoma, pancreatic adenocarcinoma, ovarian cystadenocarcinoma, mesothelioma, lung squamous cell carcinoma, lung adenocarcinoma, liver hepatocellular carcinoma, kidney papillary cell carcinoma, kidney clear cell carcinoma, kidney chromophobe carcinoma, renal cell carcinoma, head and neck squamous cell carcinoma, glioblastoma multiforme, diffuse large B-cell lymphoma, colon adenocarcinoma, cholangiocarcinoma, cervical and/or endocervical cancer, breast invasive carcinoma, brain low grade glioma, bladder cancer, or acute myeloid leukemia, and wherein said cancer expresses said ligand of KLRG1.

24. The method of any of claims 1-13, wherein the subject has a melanoma, and wherein said melanoma expresses said ligand of KLRG1.

25. The method of any of claims 1-13, wherein the subject has a lung cancer, and wherein said cancer expresses said ligand of KLRG1.

26. The method of claim 25, wherein the lung cancer is non-small cell lung cancer (NSCLC).

27. The method of any of claims 1-13, wherein the subject has a pancreatic cancer, and wherein said cancer expresses said ligand of KLRG1.

28. The method of any of claims 1-13, wherein the subject has a glioma, and wherein said cancer expresses said ligand of KLRG1.

29. The method of any of claims 1-13, wherein the subject has a breast cancer, and wherein said cancer expresses said ligand of KLRG1.

30. The method of any of claims 1-13, wherein the subject has an ovarian cancer, wherein said cancer expresses said ligand of KLRG1.

31. The method of claim 1, wherein the subject has a kidney cancer, and wherein said kidney cancer expresses said ligand of KLRG1.

32. The method of claim 31, wherein the subject has a kidney cancer, and wherein said kidney cancer expresses said ligand of KLRG1.

33. A method of treating a melanoma comprising administering to a subject in need thereof an effective amount of a killer cell lectin-like receptor G1 (KLRG1) binding agent, wherein the binding agent is an antibody or antigen binding fragment thereof, or antibody mimetic that binds the extracellular domain of human KLRG1, thereby disrupting KLRG1 signaling and activating CD8+ cytotoxic T cells.

34. A method of treating a lung cancer comprising administering to a subject in used thereof an effective amount of a killer cell lectin-like receptor G1 (KLRG1) binding agent, wherein the binding agent is an antibody or antigen binding fragment thereof, or antibody mimetic that binds the extracellular domain of human KLRG1, thereby disrupting KLRG1 signaling and activating CD8+ cytotoxic T cells.

35. The method of claim 34, wherein the lung cancer is non-small cell lung cancer (NSCLC).

36. A method of treating a pancreatic cancer comprising administering to a subject in need thereof an effective amount of a killer cell lectin-like receptor G1 (KLRG1) binding agent, wherein the binding agent is an antibody or antigen binding fragment thereof, or antibody mimetic that binds the extracellular domain of human KLRG1 thereby disrupting KLRG1 signaling and activating CD8+ cytotoxic T cells.

37. A method of treating a glioma comprising administering to a subject in need thereof an effective amount of a killer cell lectin-like receptor G1 (KLRG1) binding agent, wherein the binding agent is an antibody or antigen binding fragment thereof, or antibody mimetic that binds the extracellular domain of human KLRG1, thereby disrupting KLRG1 signaling and activating CD8+ cytotoxic T cells.

38. A method of treating a breast cancer comprising administering to a subject in need thereof an effective amount of a killer cell lectin-like receptor G1 (KLRG1) binding agent, wherein the binding agent is an antibody or antigen binding fragment thereof, or antibody mimetic that binds the extracellular domain of human KLRG1, thereby disrupting KLRG1 signaling and activating CD8+ cytotoxic T cells.

39. A method of treating an ovarian cancer comprising administering to a subject in need thereof an effective amount of a killer cell lectin-like receptor G1 (KLRG1) binding agent, wherein the binding agent is an antibody or antigen binding fragment thereof, or antibody mimetic that binds the extracellular domain of human KLRG1, thereby disrupting KLRG1 signaling and activating CD8+ cytotoxic T cells.

40. A method of treating a kidney cancer comprising administering to a subject in need thereof an effective amount of a killer cell lectin-like receptor G1 (KLRG1) binding agent, wherein the binding agent is an antibody or antigen binding fragment thereof, or antibody mimetic that binds the extracellular domain of human KLRG1, thereby disrupting KLRG1 signaling and activating CD8+ cytotoxic T cells.

41. The method of claim 40, wherein the subject has a kidney cancer, and wherein said kidney cancer expresses said ligand of KLRG1.

* * * * *

UNITED STATES PATENT AND TRADEMARK OFFICE
CERTIFICATE OF CORRECTION

| | | |
|---|---|---|
| PATENT NO. | : 11,339,222 B2 | |
| APPLICATION NO. | : 16/306473 | |
| DATED | : May 24, 2022 | |
| INVENTOR(S) | : Steven Greenberg et al. | |

It is certified that error appears in the above-identified patent and that said Letters Patent is hereby corrected as shown below:

In the Claims

At Column 42, Claim number 14, Line number 52, please change "non: transformed cells" to --non-transformed cells--

Signed and Sealed this
Twenty-eighth Day of March, 2023

Katherine Kelly Vidal
*Director of the United States Patent and Trademark Office*